US006908934B2

(12) United States Patent
Adams et al.

(10) Patent No.: US 6,908,934 B2
(45) Date of Patent: Jun. 21, 2005

(54) THERAPEUTIC COMPOUNDS FOR TREATING DYSLIPIDEMIC CONDITIONS

(75) Inventors: Alan D. Adams, Cranford, NJ (US); Aileen Bouffard, Scotch Plains, NJ (US); James F. Dropinski, Colts Neck, NJ (US); Clare E. Gutteridge, Dover, NH (US); A. Brian Jones, Harlow (GB); Weiguo Lui, Princeton, NJ (US); John George Ondeyka, Fanwood, NJ (US); Ali Shiafee, Westfield, NJ (US); Sheo Bux Singh, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 243 days.

(21) Appl. No.: 10/158,679

(22) Filed: May 30, 2002

(65) Prior Publication Data

US 2003/0125357 A1 Jul. 3, 2003

Related U.S. Application Data

(60) Provisional application No. 60/297,400, filed on Jun. 11, 2001.

(51) Int. Cl.$^7$ ..................... A01N 43/40; A61K 31/445

(52) U.S. Cl. ..................... 514/325; 564/123; 564/134; 564/139; 564/52; 514/423; 514/432; 514/533; 514/569; 514/434; 514/431; 548/195; 548/407; 548/528; 560/8; 540/490

(58) Field of Search ..................... 514/431, 432, 514/325, 434, 533, 569, 423; 546/156, 203; 548/528; 564/123, 134, 139, 52; 560/8; 540/490

(56) References Cited

U.S. PATENT DOCUMENTS

| 6,096,917 A | * | 8/2000 | Hornback et al. | ............. 560/43 |
| 6,100,426 A | * | 8/2000 | Mauldin et al. | ............. 562/440 |
| 6,124,494 A | * | 9/2000 | Mauldin et al. | ............. 560/43 |
| 6,180,815 B1 | * | 1/2001 | Mauldin et al. | ............. 560/5 |

FOREIGN PATENT DOCUMENTS

| EP | 0806203 | * | 11/1997 | ......... A61K/31/015 |
| WO | WO 97/42154 | * | 11/1997 | ......... C07C/69/753 |
| WO | WO 01/41704 | * | 6/2001 | |

OTHER PUBLICATIONS

Young et al., "The ABCs of cholesterol efflux", Nature Genetics, vol. 22, pp. 316–318 (Aug. 1999).
Bodzioch et al., "The gene encoding ATP–binding cassette transporter I is mutated in Tangier disease", nature Genetics, vol. 22, pp. 347–351 (Aug. 1999).
Brooks–Wilson et al., "Mutation in ABC1 in Tangier disease and familial high–density lipoprotein deficiency", Nature Genetics, vol. 22, pp. 336–345 (Aug. 1999).

Rust et al., "Tangier disease is caused by mutations in the gene encoding ATP–binding cassette transporter 1", Nature Genetics, vol. 22, pp. 352–355 (Aug. 1999).
Langmann et al., "Molecular Cloning of athe Human ATP–Binding Cassette Transporter 1 (hABC1): Evidence for Sterol–Dependent Regulation in Macrophanges", Biochemical and Biophysical Research Communications, vol. 257, pp. 29–33 (1999).
Peet et al., "Cholesterol and Bile Acid Metabolism are Impaired in Mice Lacking the Nuclear Oxysterol Receptor LXR alpha", Cell, vol. 93, pp. 693–704 (May 1998).
Janowski et al., "Structural requirements of ligands for the oxysterol liver X receptors LXR alpha and LXR beta", Proc. Natl. Acad. Sci. USA, vol. 96, pp. 266–271 (Jan. 1999).
Spencer et al., "Pharmacophore Analysis of the Nuclear Oxysterol Receptor LXR alpha", J. Med. Chem., vol. 44, pp. 886–897 (2001).

(Continued)

*Primary Examiner*—Johann Richter
*Assistant Examiner*—Chukwuma Nwaonichia
(74) *Attorney, Agent, or Firm*—Carol S. Quagliato; Melvin Winokur

(57) ABSTRACT

Compounds of Formula I

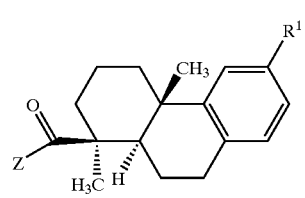

I and the pharmaceutically acceptable salts and esters thereof, wherein Z is selected from the group consisting of:

(a) Formula Ia

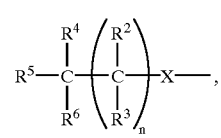

Ia and
(b) Formula Ib

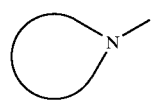

Ib are novel LXR agonists and are useful in the treatment of dyslipidemic conditions particularly depressed levels of HDL cholesterol.

26 Claims, No Drawings

OTHER PUBLICATIONS

Schultz et al., "Role of LXRs in control of lopgenesis", Genes & Development, vol. 14, pp. 2831–2838 (2000).

Repa et al., "Regulation of Absorption and ABC1–Mediated Efflux of Cholesterol by RXR Heterodimers", Science, vol. 289, pp. 1524–1529 (2000).

* cited by examiner

THERAPEUTIC COMPOUNDS FOR TREATING DYSLIPIDEMIC CONDITIONS

The instant application claims priority under 35 U.S.C. 119(e) to U.S. Provisional Application No. 60/297,400, filed Jun. 11, 2001.

BACKGROUND OF THE INVENTION

Recent publications in Nature Genetics, August, 1999 (Young et al, page 316; Bodzioch et al, page 347; Brooks-Wilson et al, page 335, and Rust et al, page 352) showed that humans with mutations in the gene ABCA1 (also previously known in the art as ABC1) have low levels of high density lipoprotein (HDL). Low HDL levels are a risk factor for atherosclerosis, myocardial infarction and related conditions such as ischemic stroke. Therefore, increasing the expression of the ABCA1 gene would be expected to increase HDL levels and decrease the occurrence of atherosclerosis, myocardial infarction and related conditions such as ischemic stroke. It has been reported that expression of the ABCA1 gene is increased by cholesterol loading of cells (Langmann et al, *Biochem. Biophys. Res. Comm.*, 257, 29–33 (1999)). LXRα is a nuclear receptor that is required for the induction of cholesterol 7α-hydroxylase in mouse liver following cholesterol feeding (Peet et al, *Cell*, 93, 693–704 (1998)). LXRα and LXRβ are activated by 22-(R)-hydroxycholesterol and other oxysterols (Janowski et al. *Proc. Natl. Acad. Sci USA*, 96, 266–271 (1999), Thomas A. Spencer et al. *J. Med. Chem.*, 44, 886–897, (2001)). Some non-steroidal small molecule agonists of LXRα and LXRβ have been reported to affect circulating HDL levels, cholesterol absorption, reverse cholesterol transport and ABCA1 expression in vivo (J. R. Schultz, et al. *Genes & Devel.* 14, 2831–2838, (2000), J. J. Repa et al. *Science,* 289, 1524–1529, (2000)) It has been found that LXRα and/or LXRβ cause the induction or regulation of ABCA1 expression, and that small molecule ligands of LXR are useful as drugs to increase the expression of ABCA1, increase levels of HDL and thereby decrease the risk of atherosclerosis, myocardial infarction and related conditions such as peripheral vascular disease and ischemic stroke.

The various dyslipidemic conditions, which are risk factors for atherosclerosis, are currently treated with several different classes of drugs, such as statins which are HMG-CoA reductase inhibitors, bile acid sequestrants (e.g., cholestyramine and colestipol), nicotinic acid (niacin), and fibrates. However, except for niacin, most of these treatments do not raise HDL as their primary effect. With favorable outcomes in many human studies, the statin class of drugs is used to modulate LDL and, to a lesser extent, HDL and triglycerides. Conditions principally characterized by elevated plasma triglycerides and low HDL are frequently treated with drugs belonging to the fibrate class. The fibrates are PPAR alpha agonists that lower triglycerides and raise HDL in many instances. There are no currently marketed drugs whose principal actions are mediated by LXR.

We have now discovered a new class of small molecules which are LXR ligands, i.e., LXRα and/or LXRβ ligands, and are therefore expected to be useful for modulation of ADL levels, ABCA1 gene expression and reverse cholesterol transport. The instant compounds have been shown to raise plasma levels of HDL in animal models and to increase cholesterol efflux from cells in vitro. These biological activities are critical for reverse cholesterol transport.

The novel compounds of this invention are intended as a treatment for dyslipidemias, especially low plasma HDL cholesterol levels, as well as for treatment and/or prevention of lipid accumulation in atherosclerotic plaques, which is an underlying cause or aggravating factor in atherosclerosis.

SUMMARY OF THE INVENTION

Compounds of Formula I are novel LXR agonists and are useful in the treatment of dyslipidemic conditions including below-desirable levels of HDL cholesterol.

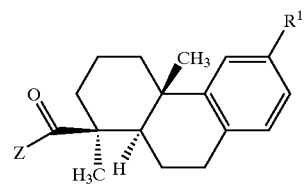

I

One object of the instant invention is to provide a method for treating depressed plasma HDL cholesterol levels comprising administering a therapeutically effective amount of a compound of Formula I to a patient in need of such treatment.

Another object is to provide a method for preventing or treating dyslipidemic conditions comprising administering a prophylactically or therapeutically effective amount, as appropriate, of a compound of Formula I to a patient in need of such treatment.

As a further object, methods are provided for preventing or reducing the risk of developing atherosclerosis, as well as for halting or slowing the progression of atherosclerotic disease once it has become clinically evident, comprising the administration of a prophylactically or therapeutically effective amount, as appropriate, of a compound of Formula I to a patient who is at risk of developing atherosclerosis or who already has atherosclerotic disease. The method of this invention also serves to remove cholesterol from tissue deposits such as xanthomas and atherosclerotic lesions by hastening the efflux of cholesterol from cells in those lesions. Additional objects will be evident from the following detailed description.

Other objects of this invention are to provide processes for making the compounds of Formula I and to provide novel pharmaceutical compositions comprising these compounds. Additional objects will be evident from the following detailed description.

DETAILED DESCRIPTION OF THE INVENTION

The novel LXR agonists of the instant invention are compounds of Formula I

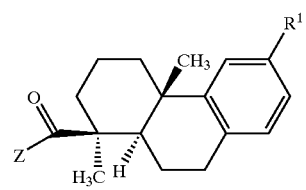

I and the pharmaceutically acceptable salts and esters thereof, wherein

Z is selected from the group consisting of:

(a) Formula Ia

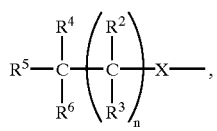

and
(b) Formula Ib

wherein Formula Ib represents a saturated heterocyclic ring containing one tertiary nitrogen atom and 5 or 6 carbon atoms, wherein each carbon atom is independently unsubstituted or substituted with at least one substituent selected from the group consisting of:
(i) —$C_{1-4}$ alkyl,
(ii) phenyl, unsubstituted or substituted with at least one —$C_{1-4}$ alkyl substituent,
(iii) —$CH_2$-phenyl, wherein phenyl is unsubstituted or substituted with at least one —$C_{1-4}$ alkyl substituent,
(iv) —COOH and
(v) —COO$C_{1-4}$ alkyl;
X is selected from the group consisting of:
(a) —NH,
(b) —O— and
(c) —$CH_2$—;
$R^1$ is selected from the group consisting of:
(a) —H,
(b) —OH and
(c) —OC(O)$CH_3$;
$R^2$ and $R^3$ are independently selected from the group consisting of:
(a) —H and
(b) —$C_{1-4}$ alkyl,
or $R^2$ and $R^3$ together represent =O;
n is an integer selected from zero and 1;
$R^4$ and $R^5$ represent moieties selected from those defined in the following groups:
(a) $R^4$ and $R^5$ are independently selected from the group consisting of
(i) —H and
(ii) phenyl, unsubstituted or substituted with a group selected from halo, —$C_{1-4}$ alkyl and —O—$C_{1-4}$ alkyl,
(b) $R^4$ and $R^5$ together represent —$(CH_2)_m$— which joins together with the carbon in Formula Ia to which $R^4$ and $R^5$ are commonly attached to form a cycloalkyl ring, and wherein m is an integer selected from 2 through 5,
(c) $R^4$ and $R^5$ are each alkyl groups joined together with the carbon in Formula Ia to which they are commonly attached to form a carbon-bridged polycycloalkyl ring system selected from isopinylcampheyl and adamantyl, wherein the ring system is unsubstituted or substituted with —$C_{1-4}$ alkyl,
(d) $R^4$, $R^5$ and $R^6$ are each alkyl groups joined together with the carbon in Formula Ia to which they are commonly attached to form a carbon-bridged polycycloalkyl ring system which is adamantyl, wherein the ring system is unsubstituted or substituted with —$C_{1-4}$ alkyl, and
(e) $R^4$, $R^5$ and $R^6$ together with the carbon in Formula Ia to which they are commonly attached represent

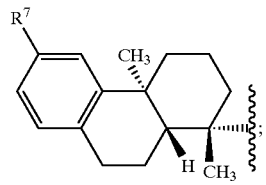

provided $R^6$ is not joined together with $R^4$ and $R^5$ as described above, then $R^6$ is selected from the group consisting of:
(a) —H and
(b) phenyl, unsubstituted or substituted with a group selected from halo, —$C_{1-4}$ alkyl and —O—$C_{1-4}$ alkyl,
except that when $R^4$ and $R^5$ are each alkyl groups joined together with the carbon in Formula Ia to which they are commonly attached to form a carbon-bridged polycycloalkyl ring system, then $R^6$ is —H;
$R^7$ is selected from the group consisting of:
(a) —H,
(b) —OH and
(c) —OC(O)$CH_3$; and
provided that when n is 1, and $R^2$ and $R^3$ together represent =O, and $R^4$, $R^5$ and $R^6$ together with the carbon in Formula I to which they are commonly attached represent

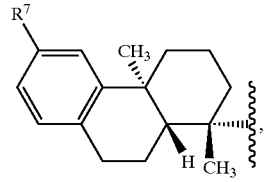

and $R^1$ is —OC(O)$CH_3$ and $R^7$ is —OC(O)$CH_3$, then X is not —O—.

In one embodiment of this invention are compounds of Formula I wherein Z is Formula Ia. In one class of this embodiment are compounds wherein X is —NH—. Specific examples within this class are defined for Formula I in Table 1.

TABLE 1

| | $R^1$ | Z |
|---|---|---|
| (a) | —OH | ![structure] |
| (b) | —OAc | ![structure] |

TABLE 1-continued

| | R¹ | Z |
|---|---|---|
| (c) | —OH | 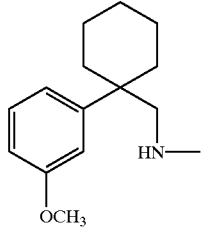 |
| (d) | —OH | 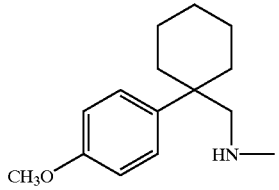 |
| (e) | —OH | 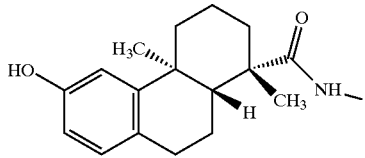 |
| (f) | —OH | 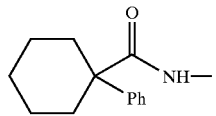 |
| (g) | —OH | 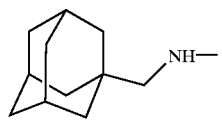 |
| (h) | —OH | 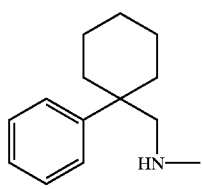 |
| (i) | —H | 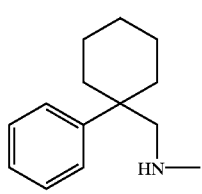 |
| (j) | —OH | 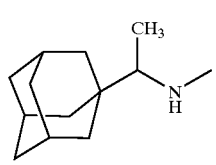 |

TABLE 1-continued

| | R¹ | Z |
|---|---|---|
| (k) | —OH | 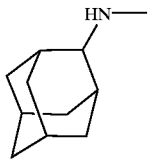 |
| (l) | —OH | 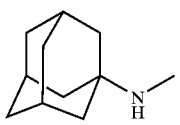 |
| (m) | —OH | 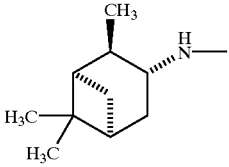 |

In a sub-class of the first class are compounds wherein X is —NH—, n is one, $R^4$ and $R^5$ together represent —(CH$_2$)$_m$— which joins together with the carbon in Formula Ia to which $R^4$ and $R^5$ are commonly attached to form a cycloalkyl ring, and wherein m is an integer selected from 3 through 5, and $R^6$ is phenyl, unsubstituted or monosubstituted with a group selected from halo, —C$_{1-4}$ alkyl and —O—C$_{1-4}$ alkyl. Specific examples within this class are shown in Table 1, compounds (a), (c), (d) (f), (h), and (i).

In a second class of the first embodiment are compounds wherein X is —O—. Specific examples within this class are defined for Formula I in Table 2.

TABLE 2

| | R¹ | Z |
|---|---|---|
| (a) | —OH | 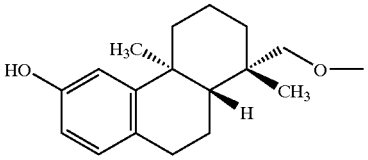 |
| (b) | —OAc | 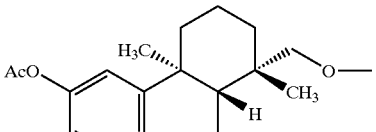 |
| (c) | —OH | 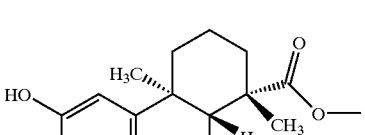 |

In a third class of the first embodiment are compounds wherein X is —CH2—. Specific examples within this class are defined for Formula I in Table 3.

TABLE 3

| | R¹ | Z |
|---|---|---|
| (a) | —OH | 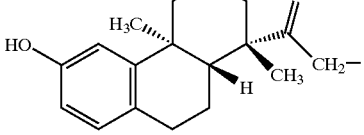 |
| (b) | —OH | 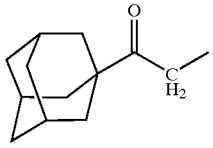 |

In a fourth class of the first embodiment are compounds wherein R² and R³ together represent =O; and R⁴, R⁵ and R⁶ together with the carbon in Formula Ia to which they are commonly attached represent:

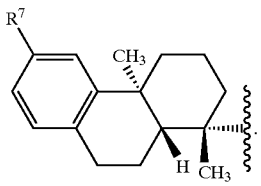

Specific examples within this class are shown in Table 1, compound (e); Table 2, compound (c); and Table 3, compound (a).

In a second embodiment of this invention are compounds of Formula I wherein Z is Formula Ib. Specific examples within this class are defined for Formula I in Table 4.

TABLE 4

| | R¹ | Z |
|---|---|---|
| (a) | —OH | 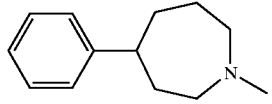 |
| (b) | —OH | 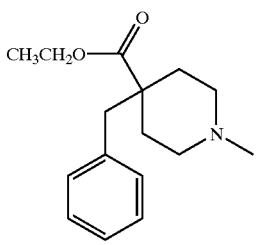 |
| (c) | —OH | 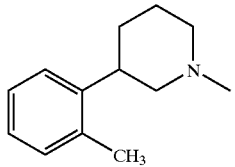 |

TABLE 4-continued

| | R¹ | Z |
|---|---|---|
| (d) | —OH | 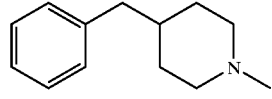 |

One class of compounds within the second embodiment are those wherein Formula Ib is a saturated seven-membered heterocyclic ring containing one tertiary nitrogen atom and six carbon atoms, wherein each carbon atom is independently unsubstituted or mono-substituted with a substituent selected from the group consisting of: (i)—$C_{1-4}$ alkyl, (ii) phenyl, unsubstituted or substituted with at least one —$C_{1-4}$ alkyl substituent, (iii) —$CH_2$-phenyl, wherein phenyl is unsubstituted or substituted with at least one —$C_{1-4}$ alkyl substituent, (iv) —COOH and (v) —COO$C_{1-4}$ alkyl. A specific example within this class is shown in Table 4, compound (a).

As used herein "alkyl" is intended to include both branched- and straight-chain saturated aliphatic hydrocarbon groups having the specified number of carbon atoms, e.g., methyl (Me), ethyl (Et), propyl (Pr), butyl (Bu), pentyl, hexyl, and the isomers thereof such as isopropyl (i-Pr), isobutyl (i-Bu), secbutyl (s-Bu), tertbutyl (t-Bu), isopentyl, isohexyl and the like. The term "cycloalkyl" is intended to include cyclized alkyl chains having the specified number of carbon atoms, e.g., cyclopropyl, cyclobutyl, cyclopentyl and cyclohexyl.

A carbon-bridged polycycloalkyl ring system is intended to include cycloalkyl rings having one or more alkyl chains bridging between non-adjacent cycloalkyl carbons so as to form two or more fused rings, and having the specified number of carbon atoms. Examples include isopinylcampheyl and adamantyl.

In Formula I, when Z is Formula Ia and R⁴ and R⁵ are each alkyl groups joined together with the carbon in Formula Ia to which they are commonly attached ("the common carbon") to form a carbon-bridged polycycloalkyl ring system selected from isopinylcampheyl and adamantyl, it is intended that the common carbon is bonded to two other carbon atoms which are integral in the polycycloalkyl ring system, for example:

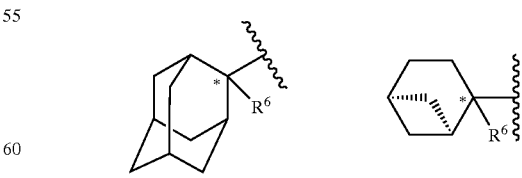

wherein the common carbon is denoted with an asterisk.

In Formula I, when Z is Formula Ia and R⁴, R⁵ and R⁶ are each alkyl groups joined together with the carbon in Formula Ia to which they are commonly attached ("the common carbon") to form a carbon-bridged polycycloalkyl ring system which is adamantyl, it is intended that the common carbon is bonded to three other carbon atoms which are integral in the adamantyl polycycloalkyl ring system, for example:

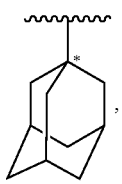

wherein the common carbon is denoted with an asterisk.

For clarity, the carbon referred to herein as the "common carbon" in Formula Ia is denoted below with an asterisk:

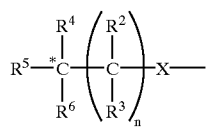

The term halo or halogen is meant to include fluoro, chloro, bromo and iodo, unless otherwise noted. Fluoro is preferred.

When referring to moieties which may optionally be substituted herein, e.g., alkyl groups, phenyl and the like, it is intended to mean that each atom that is available for substitution in the given moiety may independently be unsubstituted or substituted, and substituted atoms may have one or more substituents that are the same or different and which result in the creation of a stable structure. Particularly, each moiety that can be optionally substituted is mono-, di- or tri-substituted, more particularly is mono- or di-substituted, and most particularly is mono-substituted, while each available atom in the moiety may be mono- or di-substituted, and most particularly is mono-substituted.

Some abbreviations used herein are as follows: Ac is acetyl [$CH_3C(O)$—]; PG is protecting group; Ph is phenyl; PhMe is toluene; Bn is benzyl; BnBr is benzylbromide; MeOH is methanol; DMF is N,N-dimethylformamide; DMSO is dimethyl sulfoxide; THF is tetrahydrofuran; TMS is trimethylsilyl; HOBt is 1-hydroxybenzotriazole; EDAC (or EDC) is 1-ethyl-3-[3-(dimethylamino)propyl] carbodiimide HCl; NaHMDS is sodium hexamethyldisiliazide; DIBAL is diisobutylaluminum hydride; TPAP is tetrapropylammonium perruthenate; NMO is N-methylmorpholine N oxide; HPLC is high performance liquid chromatography; TLC is thin layer chromatography; RT is ambient temperature.

The compounds of the present invention are chiral and the present compounds may occur as diastereomeric mixtures, racemates and racemic mixtures, and as individual enantiomers or diasteriomers with all such isomeric forms being included within the scope of this invention, except where the stereoconfiguration of a specific chiral center is defined or depicted otherwise. Furthermore, some of the crystalline forms for compounds of the present invention may exist as polymorphs and as such are intended to be included in the present invention. In addition, some of the compounds of the instant invention may form solvates with water or common organic solvents. Such solvates and hydrates are encompassed within the scope of this invention.

The compounds of this invention can be made employing the following general procedures. Commercially available podocarpic acid [(4β,5α)-12-hydroxypodocarpa-8,11,13-trien-16-oic acid] is first elaborated into a suitable coupling partner. This may be carried out as shown below in Scheme 1, wherein the acid is esterified, here exemplified by the methyl ester. This allows protection of the phenol group, here exemplified as the benzyl ether. Removal of the ester by base-mediated hydrolysis restores the acid functionality, thereby giving a useful podocarpic acid intermediate.

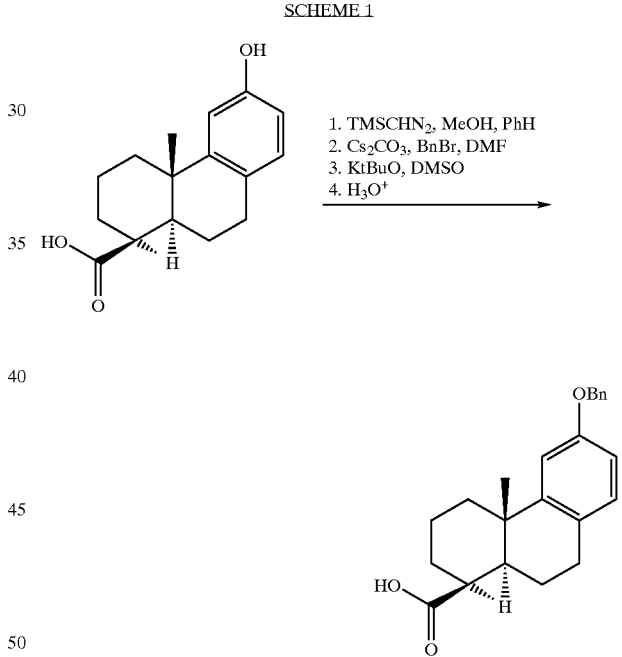

The acid group of this compound can be activated to enable reaction with a variety of amine-containing compounds. Many methods are known in the literature to effect this activation; depicted below in Scheme 2 is the use of a particular carbodiimide reagent to prepare an intermediate 1-hydroxybenzotriazole ester (Step 1), which can undergo reaction with a range of amines. Preparation of the required amines is readily done by practitioners in the field of synthetic organic chemistry. Further standard synthetic methods can be used to manipulate the substituent on the phenol, for instance, deprotection to yield the free phenol (Step 3).

SCHEME 2

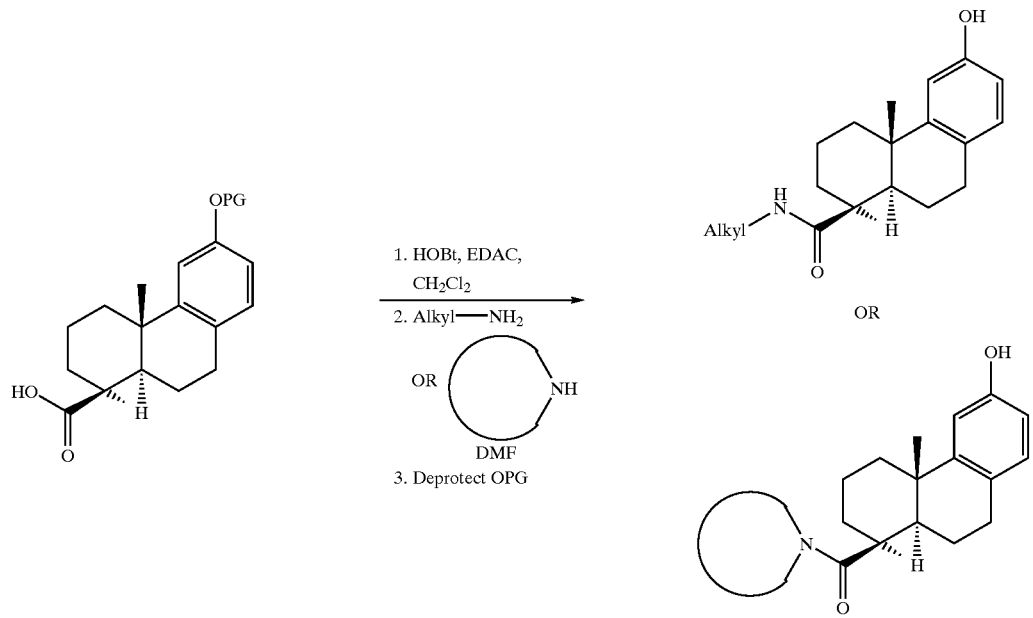

A range of possible reactions can derivatize the resulting phenol, for instance, treatment with acetic anhydride will yield the acetyl derivative (not depicted).

Moreover, the phenolic —OH can be replaced by —H, by treatment with diethyl chlorophosphate, followed by lithium in ammonia, as depicted in Scheme 3

SCHEME 3.

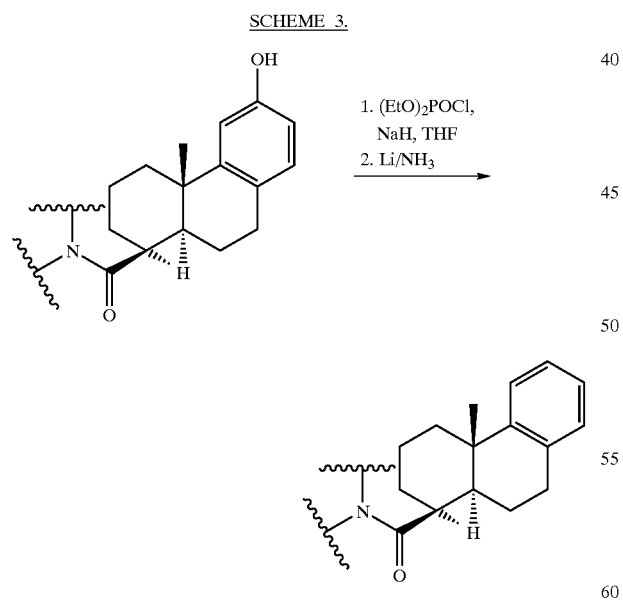

The podocarpic acid intermediate may also be dimerized using related chemical methods. For instance as shown below in Scheme 4, reaction with the carbodiimide alone (Step 1) provides the anhydride derivative depicted below (after benzyl removal, Step 2).

SCHEME 4

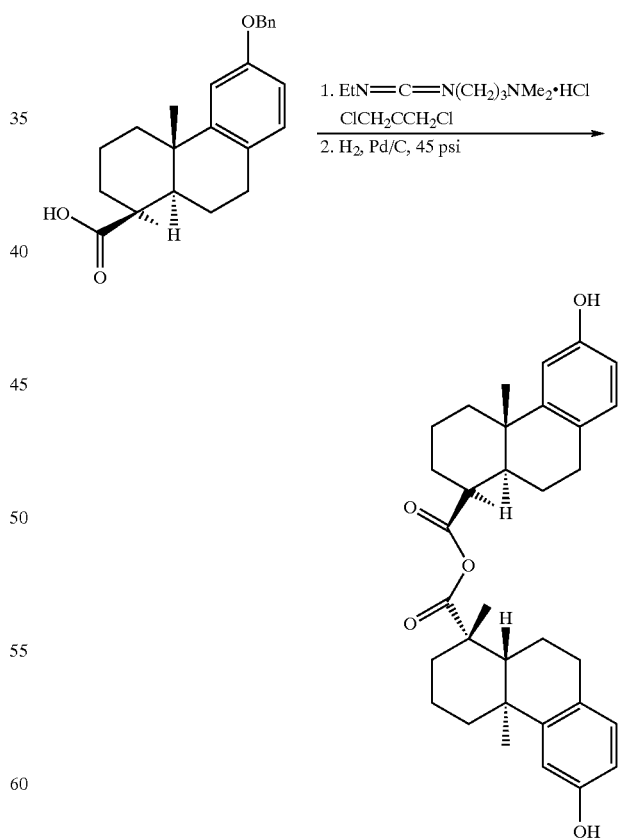

Alternative processing of the podocarpic acid intermediate can yield dimeric materials wherein the linker is structurally different. For example an imide may be prepared in the following manner: the acid may be converted to the corresponding acyl chloride by a variety of methods, including the use of thionyl chloride. Subsequent reaction with ammonia yields the amide. Treatment of this with a base such as sodium hexamethyldisiliazide, followed by reaction with a second equivalent of the podocarpic acid chloride, gives after hydrogenolysis of the benzyl ether the target imide. This procedure is exemplified in Scheme 5, below.

SCHEME 5

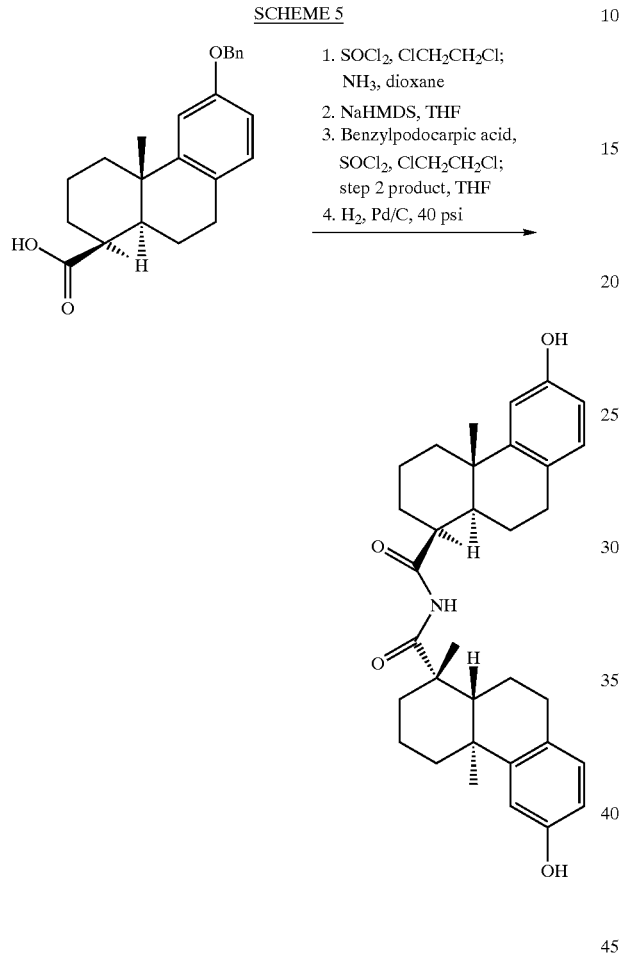

1. SOCl$_2$, ClCH$_2$CH$_2$Cl; NH$_3$, dioxane
2. NaHMDS, THF
3. Benzylpodocarpic acid, SOCl$_2$, ClCH$_2$CH$_2$Cl; step 2 product, THF
4. H$_2$, Pd/C, 40 psi An ester-linked compound can be prepared similarly. The benzylated podocarpate methyl ester can be reduced to the corresponding alcohol, for instance by treatment with lithium aluminium hydride. Reaction of this material with the acid chloride described above followed by removal of the benzyl ether provides a route to target structure. This procedure is exemplified in Scheme 6, below.

SCHEME 6

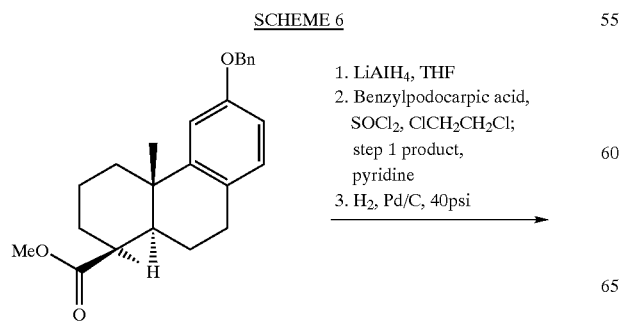

1. LiAlH$_4$, THF
2. Benzylpodocarpic acid, SOCl$_2$, ClCH$_2$CH$_2$Cl; step 1 product, pyridine
3. H$_2$, Pd/C, 40psi

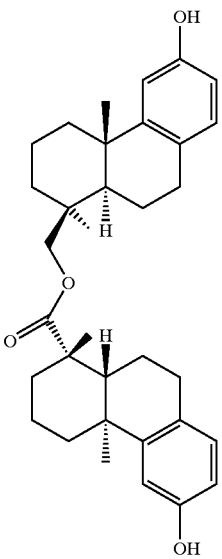

Alternatively the benzylated podocarpate methyl ester can be converted to the corresponding methyl ketone via reduction to the corresponding alcohol, oxidation to the aldehyde, methylation and a second oxidation. Reaction of the sodium enolate of this ketone with an acid chloride, followed by removal of the benzyl ether, supplies a diketone-linked structure. This procedure is exemplified in Scheme 7, below.

SCHEME 7

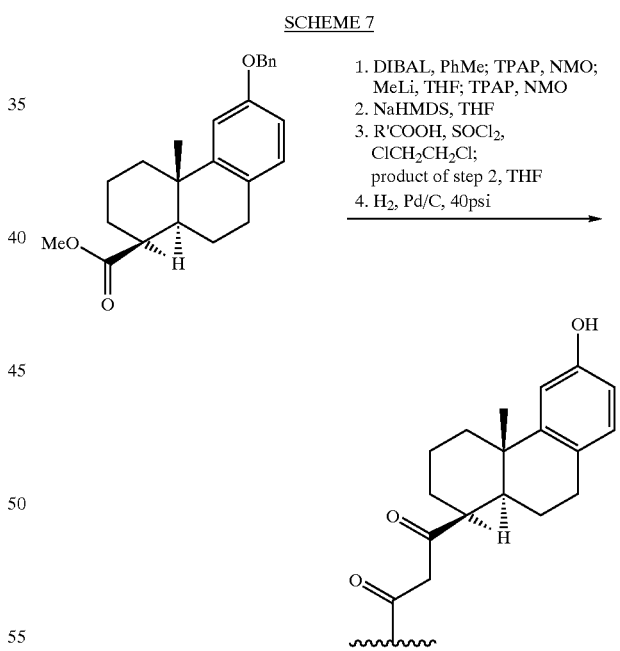

1. DIBAL, PhMe; TPAP, NMO; MeLi, THF; TPAP, NMO
2. NaHMDS, THF
3. R'COOH, SOCl$_2$, ClCH$_2$CH$_2$Cl; product of step 2, THF
4. H$_2$, Pd/C, 40psi The instant invention provides methods for treating lipid disorders, particularly for treating below-desired plasma HDL cholesterol levels, raising HDL cholesterol levels, and for treating and/or reducing the risk for diseases and conditions affected by LXR activity, comprising administering a therapeutically effective amount of a compound of Formula I to a person in need of such treatment. Any patient having a depressed plasma HDL cholesterol level, or desiring to increase their HDL cholesterol level may use this treatment. Particularly suitable patients in need of such treatment are those whose plasma HDL cholesterol level is depressed, i.e., below the clinically desirable level. Currently, the clinically desirable HDL cholesterol level is considered to be about 40 mg/dl or higher in men and about 50 mg/dl or higher in women.

The method of this invention also serves to prevent lipid accumulation in, or remove cholesterol from, tissue deposits such as atherosclerotic plaques or xanthomas in a patient with atherosclerotic disease manifest by clinical signs such as angina, claudication, bruits, one that has suffered a myocardial infarction or transient ischemic attack, or one diagnosed by angiography, sonography or MRI.

Further provided are methods for preventing or reducing the risk of developing atherosclerosis, as well as for halting or slowing the progression of atherosclerotic disease once it has become clinically evident, comprising the administration of a prophylactically or therapeutically effective amount, as appropriate, of a compound of Formula I to a mammal, including a human, who is at risk of developing atherosclerosis or who already has atherosclerotic disease.

Atherosclerosis encompasses vascular diseases and conditions that are recognized and understood by physicians practicing in the relevant fields of medicine. Atherosclerotic cardiovascular disease including restenosis following revascularization procedures, coronary heart disease (also known as coronary artery disease or ischemic heart disease), cerebrovascular disease including multi-infarct dementia, and peripheral vessel disease including erectile dysfunction are all clinical manifestations of atherosclerosis and are therefore encompassed by the terms "atherosclerosis" and "atherosclerotic disease."

A compound of Formula I may be administered to prevent or reduce the risk of occurrence, or recurrence where the potential exists, of a coronary heart disease event, a cerebrovascular event, and/or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists.

Accordingly, the instant invention also provides a method for preventing or reducing the risk of a first or subsequent occurrence of an atherosclerotic disease event comprising the administration of a prophylactically effective amount of a compound of Formula I to a patient at risk for such an event. The patient may or may not have atherosclerotic disease at the time of administration, or may be at risk for developing it.

Persons to be treated with the instant therapy include those with dyslipidemic conditions including depressed or below-desirable plasma levels of HDL cholesterol, as well as those at risk of developing atherosclerotic disease and of having an atherosclerotic disease event. Standard atherosclerotic disease risk factors are known to the average physician practicing in the relevant fields of medicine. Such known risk factors include but are not limited to hypertension, smoking, diabetes, low levels of high density lipoprotein cholesterol, and a family history of atherosclerotic cardiovascular disease. Published guidelines for determining those who are at risk of developing atherosclerotic disease can be found in: National Cholesterol Education Program, Second report of the Expert Panel on Detection, Evaluation, and Treatment of High Blood Cholesterol in Adults (Adult Treatment Panel II), National Institute of Health, National Heart Lung and Blood Institute, NIH Publication No. 93-3095, September 1993; abbreviated version: Expert Panel on Detection, Evaluation, and Treatment of High Blood Cholesterol in Adults, Summary of the second report of the national cholesterol education program (NCEP) Expert Panel on Detection, Evaluation, and Treatment of High Blood Cholesterol in Adults (Adult Treatment Panel II), JAMA, 1993, 269, pp. 3015–23. People who are identified as having one or more of the above-noted risk factors are intended to be included in the group of people considered at risk for developing atherosclerotic disease. People identified as having one or more of the above-noted risk factors, as well as people who already have atherosclerosis, are intended to be included within the group of people considered to be at risk for having an atherosclerotic disease event.

The term "patient" includes mammals, especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk for diseases and medical conditions affected by HDL cholesterol.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. Particularly, the dosage amount of a compound of Formual I that a patient receives can be selected so as to achieve the amount of lipid level modification desired, particularly to achieve a desired level of HDL cholesterol. The dosage a patient receives may also be titrated over time in order to reach a target lipid profile. The dosage regimen utilizing a compound of Formula I is selected in accordance with a variety of factors including type, species, age, weight, sex and medical condition of the patient; the severity of the condition to be treated; the potency of the compound chosen to be administered; drug combinations; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition.

An effective amount of compound for use in the method of this invention is about 0.01 mg/kg to about 140 mg/kg of body weight per day, or about 0.5 mg to about 7 g per patient in single or divided doses per day. More particularly, an amount of about 0.5 mg to about 3.5 g per patient in single or divided doses per day can be administered. However, dosage amounts will vary depending on factors as noted above, including the potency of the particular compound. Although the active drug of the present invention may be administered in divided doses, for example from one to four times daily, a single daily dose of the active drug is preferred.

The active drug employed in the instant therapy can be administered in such oral forms as tablets, capsules, pills, powders, granules, elixirs, tinctures, suspensions, syrups, and emulsions. Oral formulations are preferred.

Administration of the active drug can be via any pharmaceutically acceptable route and in any pharmaceutically acceptable dosage form. This includes the use of oral conventional rapid-release, time controlled-release and delayed-release (such as enteric coated) pharmaceutical dosage forms. Additional suitable pharmaceutical compositions for use with the present invention are known to those of ordinary skill in the pharmaceutical arts; for example, see Remington's Pharmaceutical Sciences, Mack Publishing Co., Easton, Pa.

In the methods of the present invention, the active drug is typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with a non-toxic, pharmaceutically acceptable, inert carrier such as lactose, starch, sucrose, glucose, modified sugars, modified starches, methyl cellulose and its derivatives, dicalcium phosphate, calcium sulfate, mannitol, sorbitol and other reducing and non-reducing sugars, magnesium stearate, steric acid, sodium stearyl fumarate, glyceryl behenate, calcium stearate and the like. For oral administration in liquid form, the drug components can be combined with non-toxic, pharmaceutically acceptable inert carrier such as ethanol, glycerol, water and the like. Moreover, when desired or necessary, suitable binders, lubricants, disintegrating agents and coloring and flavoring agents can also be incorporated into the mixture. Stabilizing agents such as antioxidants, for example butylated hydroxyanisole (BHA), 2,6-di-tert-butyl-4-methylphenol (BHT), propyl gallate, sodium ascorbate, citric acid, calcium metabisulphite, hydroquinone, and 7-hydroxycoumarin, can also be added to stabilize the dosage forms. Other suitable components include gelatin, sweeteners, natural and synthetic gums such as acacia, tragacanth or alginates, carboxymethylcellulose, polyethylene glycol, waxes and the like.

The active drug can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Active drug may also be delivered by the use of monoclonal antibodies as individual carriers to which the compound molecules are coupled. Active drug may also be coupled with soluble polymers as targetable drug carriers. Such polymers can include polyvinyl-pyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier.

In a broad embodiment, any suitable additional active agent or agents may be used in combination with the compound of Formula I in a single dosage formulation, or may be administered to the patient in a separate dosage formulation, which allows for concurrent or sequential administration of the active agents. One or more additional active agents may be administered with a compound of Formula I. The additional active agent or agents can be lipid modifying compounds or agents having other pharmaceutical activities, or agents that have both lipid-modifying effects and other pharmaceutical activities. Examples of additional active agents which may be employed include but are not limited to HMG-CoA reductase inhibitors, which include statins in their lactonized or dihydroxy open acid forms and pharmaceutically acceptable salts and esters thereof, including but not limited to lovastatin (see U.S. Pat. No. 4,342,767); simvastatin (see U.S. Pat. No. 4,444,784); dihydroxy open-acid simvastatin, particularly the ammonium or calcium salts thereof; pravastatin, particularly the sodium salt thereof (see U.S. Pat. No. 4,346,227); fluvastatin particularly the sodium salt thereof (see U.S. Pat. No. 5,354,772); atorvastatin, particularly the calcium salt thereof (see U.S. Pat. No. 5,273,995); cerivastatin, particularly the sodium salt thereof (see U.S. Pat. No. 5,177,080), and pitavastatin also referred to as NK-104 (see PCT international publication number WO 97/23200); HMG-CoA synthase inhibitors; squalene epoxidase inhibitors; squalene synthetase inhibitors (also known as squalene synthase inhibitors), acylcoenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; probucol; niacin; cholesterol absorption inhibitors such as SCH-58235 also known as ezetimibe and 1-(4-fluorophenyl)-3(R)-[3(S)-(4-fluorophenyl)-3-hydroxypropyl)]-4(S)-(4-hydroxyphenyl)-2-azetidinone, which is described in U.S. Pat. Nos. 5,767,115 and 5,846,966; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists including the compounds commonly referred to as glitazones for example troglitazone, pioglitazone and rosiglitazone and, including those compounds included within the structural class known as thiazolidinediones as well as those PPARγ agonists outside the thiazolidinedione structural class; PPARα agonists such as clofibrate, fenofibrate including micronized fenofibrate, and gemfibrozil; PPAR dual α/γ agonists; vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan; angiotensin converting enzyme inhibitors such as enalapril and captopril; calcium channel blockers such as nifedipine and diltiazam; endothelian antagonists; agents that enhance ABCA1 gene expression; FXR ligands including both inhibitors and agonists; bisphosphonate compounds such as alendronate sodium; and cyclooxygenase-2 inhibitors such as rofecoxib and celecoxib. Additionally, the compounds of Formula I of this invention, may be used in combination with antiretroviral therapy in AIDS infected patients to treat lipid abnormalities associated with such treatment, for example but not limited to their use in combination with HIV protease inhibitors such as indinavir, nelfinavir, ritonavir and saquinavir.

A therapeutically or prophylactically effective amount, as appropriate, of a compound of Formula I can be used for the preparation of a medicament useful for treating lipid disorders, particularly for treating low HDL cholesterol levels as well as for treating and/or reducing the risk for diseases and conditions affected by agonism of LXR, preventing or reducing the risk of developing atherosclerotic disease, halting or slowing the progression of atherosclerotic disease once it has become clinically manifest, and preventing or reducing the risk of a first or subsequent occurrence of an atherosclerotic disease event. For example, the medicament may be comprised of about 0.5 mg to 7 g of a compound of Formula I, or more particularly about 0.5 mg to 3.5 g. The medicament comprised of a compound of Formula I may also be prepared with one or more additional active agents, such as those described supra.

As used herein, the term LXR includes all subtypes of this receptor. The compounds of Formula I are LXR agonists and individually may vary in their selectivity for one or the other of LXRα and LXRβ, or they may have mixed binding affinity for both LXRα and LXRβ. More particularly, the tested compounds included within the scope of this invention have an $IC_{50}$ less than or equal to 1 μM for at least one of either the LXRα or LXRβ receptors employing the LXR radioligand competition scintillation proximity assays described below in the Example section.

For clarity, the following two structural representations are chemically equivalent:

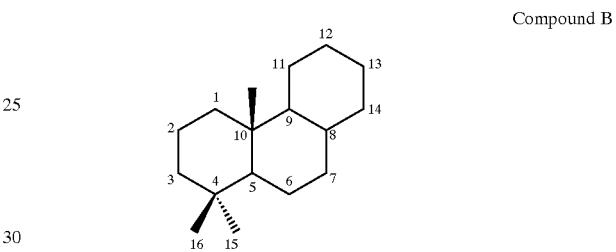

Both drawing styles are used in this application. The drawing style shown in II above (where the methyl groups are represented by bonds without the "—CH$_3$" drawn in) is primarily employed in the Examples.

Compound A is used in the following assays and has the following structural formula:

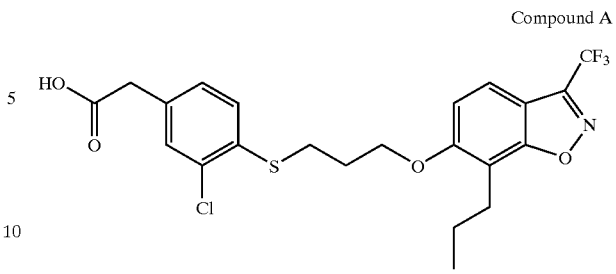

Compound A

Compound A and related compounds are disclosed along with methods for making them in WO97/28137 herein incorporated by reference in its entirety (U.S. Ser. No. 08/791211, filed Jan. 31, 1997).

Structures in the examples listed below are named and numbered by reference to the parent 10β-podocarpane nucleus, as defined by Compound B below.

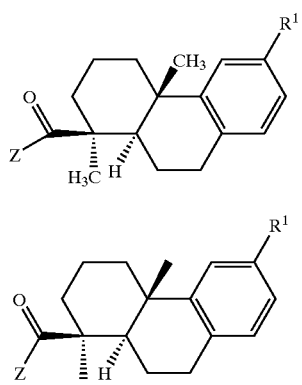

Compound B

The compounds in the following examples were characterized using $^1$H NMR at 400 or 500 MHz field strength, and/or by ESI mass spectroscopy (MS).

EXAMPLE 1

Radioligand Competition Binding Scintillation Proximity Assays:

Preparation of Recombinant Human LXRα and LXRβ:

Human LXRα and LXRβ were expressed as GST-fusion proteins in *E. coli*. The ligand binding domain cDNAs for human LXRα (amino acids 164–447) and human LXRβ (amino acids 149–455) were subcloned into the pGEX-KT expression vector (Pharmacia). *E. coli* containing the respective plasmids were propagated, induced, and harvested by centrifugation. The resuspended pellet was broken in a French press and debris was removed by centrifugation. Recombinant human LXR receptors were purified by affinity chromatography on glutathione sepharose and receptor was eluted with glutathione. Glycerol was added to a final concentration of 50% to stabilize the receptor and aliquots were stored at −80 ° C.

Binding to LXRα:

For each assay, an aliquot of human GST-LXRα receptor was incubated in a final volume of 100 μl SPA buffer (10 mM Tris, pH 7.2, 1 mM EDTA, 10% glycerol, 10 mM Na molybdate, 1 mM dithiothreitol, and 2 μg/ml benzamidine) containing 1.25 mg/ml yttrium silicate protein A coated SPA beads (Amersham Pharmacia Biotech, Inc.), 8.3 μ/ml anti-GST antibody (Amersham Pharmacia Biotech, Inc.), 0.1% non-fat dry milk and 25 nM [$^3$H$_2$]Compound A (13.4 Ci/mmole), ±test compound. After incubation for ~16 h at 15° C. with shaking, the assay plates were counted in a Packard Topcount. In this assay the $K_d$ for Compound A for LXRα is ≈15 nM.

Binding to LXRβ:

For each assay, an aliquot of human GST-LXRβ ligand binding domain receptor was incubated in a final volume of 100 μl SPA buffer (10 mM Tris, pH 7.2, 1 mM EDTA, 10% glycerol, 10 mM Na molybdate, 1 mM dithiothreitol, and 2 μg/ml benzamidine) containing 1.25 mg/ml yttrium silicate protein A coated SPA beads (Amersham Pharmacia Biotech, Inc.), 8.3 μg/ml anti-GST antibody (Amersham Pharmacia Biotech, Inc.) 0.1% non-fat dry milk and 25 nM [$^3H_2$] Compound A (13.4 Ci/mmole), ±test compound. After incubation for ~16 h at 15° C. with shaking, the assay plates were counted in a Packard Topcount. In this assay the $K_d$ for Compound A for LXRβ is ≈10 nM.

Results:

Representative tested compounds of Formula I are ligands for human LXRα and human LXRβ, each having an $IC_{50}$ less than or equal to 500 nM for the LXRα receptor, and an $IC_{50}$ less than or equal to 300 nM for the LXRβ receptor.

EXAMPLE 2

Transactivation Assay

Plasmids

Expression constructs were prepared by inserting the ligand binding domain (LBD) of human LXRα and LXRβ cDNAs adjacent to the yeast GAL4 transcription factor DNA binding domain (DBD) in the mammalian expression vector pcDNA3 to create pcDNA3-LXRα/GAL4 and pcDNA3-LXRβ/GAL4, respectively. The GAL4-responsive reporter construct, pUAS(5X)-tk-luc, contained 5 copies of the GAL4 response element placed adjacent to the thymidine kinase minimal promoter and the luciferase reporter gene. The transfection control vector, pEGFP-N1, contained the Green Fluorescence Protein (GFP) gene under the regulation of the cytomegalovirus promoter.

Assay

BEK-293 cells were seeded at 40,000 cells/well in 96 well plates in Dulbecco's modified Eagle medium (high glucose) containing 10% charcoal stripped fetal calf serum, 100 units/ml Penicillin G and 100 μg/ml Streptomycin sulfate at 37° C. in a humidified atmosphere of 5% $CO_2$. After 24 h, transfections were performed with Lipofectamine (Gibco-BRL, Gaithersburg, Md.) according to the instructions of the manufacturer. In general, transfection mixes contained 0.002 μg of LXRα/GAL4 or LXRα/GAL4 chimeric expression vectors, 0.02 μg of reporter vector pUAS(5X)-tk-luc and 0.034 μg of pEGFP-N1 vector as an internal control of transfection efficiency. Compounds were characterized by incubation with transfected cells for 48 h across a range of concentrations. Cell lysates were prepared from washed cells using Cell Lysis Buffer (Promega) according to the manufacturer's directions. Luciferase activity in cell extracts was determined using Luciferase Assay Buffer (Promega) in a ML3000 luminometer (Dynatech Laboratories). GFP expression was determined using the Tecan Spectrofluor Plus at excitation wavelength of 485 nm and emission at 535 nm. Luciferase activity was normalized to GFP expression to account for any variation in efficiency of transfection.

Results with representative tested compounds of Formula I for LXRα transactivation are $EC_{50}$ 3 to 3,000 nM, and results for LXRβ transactivation are $EC_{50}$ of 3 to 3,000 nM.

EXAMPLE 3

Induction of ABCA1 mRNA Levels

Human Primary Macrophages were used to test the ability of LXR ligands to induce the expression of ABCA1 mRNA. The collection and purification of monocytes and their subsequent differentiation into macrophages by culturing in Teflon jars for 7–9 days was performed according to Wright and Silverstein J. Exp. Med. V156, October 1982 pp 1149–1164. Cells were harvested from the Teflon jars and seeded into appropriate vessels in RPMI1640 plus 12% human serum and antibiotics. Cells were allowed to recover overnight before treatment. Treatment was for 18 hours with the described compounds, followed by a re-application of fresh compounds for an additional 6 hours in DMEM minus Phenol Red with 10% charcoal stripped FCS. The cells were harvested and total RNA prepared using the phenol/guanidine isothiocyanate method as supplied and described by Molecular Research Center, Inc. (TRI REAGENT® Cat. No. TR 118). ABCA1 mRNA levels in the total RNA were measured using the TaqMan® mRNA quantitation system, following protocols published by the manufacturer (Perkin-Elmer). The oligonucleotide PCR primers used to detect ABCA1 were:

GAGGCTCCCGGAGTTGTTG and GTATAAAA-GAAGCCTCCGAGCATC

The oligonucleotide probe used was:

6FAM-AAACTTTAACAAATCCATTGTGGCTCGCCTGT-TAMRA ABCA1 mRNA levels in each sample were normalized to the mRNA levels for the 23 kDa highly basic protein. The oligonucleotide PCR primers used to detect the 23 kDa highly basic protein were:

GCTGGAAGTACCAGGCAGTGA and ACCGG-TAGTGGATCTTGGCTTT

The oligonucleotide probe used was:

VIC-TCTTTCCTCTTCTCCTCCAGGGTGGCT-TAMRA

| Compound | Fold Induction of ABCA1 mRNA (Mean ± SEM) | P Value vs DMSO Control |
|---|---|---|
| 10 μM 22-(R)-hydroxycholesterol | 8 ± 1.37 | 0.007 |
| 0.03 μM Compound of Example 11 | 10 | 0.007 |

EXAMPLE 4

Preparation of (4β,5α)-12-Hydroxy-N-[(1-phenylcyclobutyl)methyl]podocarpa-8,11,13-trien-16-amide STEP A: Preparation of Methyl (4β,5α)-12-hydroxypodocarpa-8,11,13-trien-16-oate.

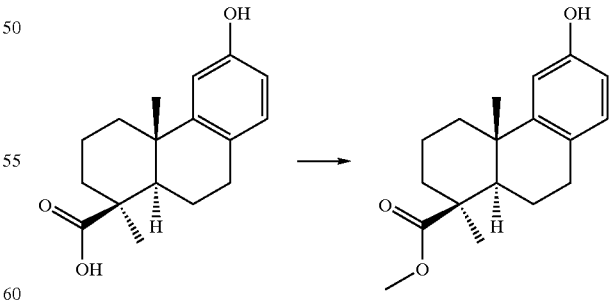

A solution of (4β,5α)-12-hydroxypodocarpa-8,11,13-trien-16-oic acid (2.1 grams) in methanol (14.0 mL) and benzene (52.0 mL) was treated with trimethylsilyldiazomethane in hexanes (4.59 mL, 2 M). This mixture was stirred overnight. A further portion of trimethylsilyldiazomethane (0.4 mL) was added. After 15 min, the solvent was evaporated and the resulting solid was chromatographed on silica gel using ethyl acetate and hexane (1:2) to give the titled compound (2.2 grams).

Selected signals $^1$H NMR (CDCl$_3$) δ 6.93 (d, 1H), 6.76 (d, 1H), 6.60 (dd, 1H), 3.68 (s, 3H), 2.85 (dd, 1H), 2.74 (m, 1H) ppm.

STEP B: Preparation of Methyl (4β,5α)-12-(benzyloxy)podocarpa-8,11,13-trien-16-oate.

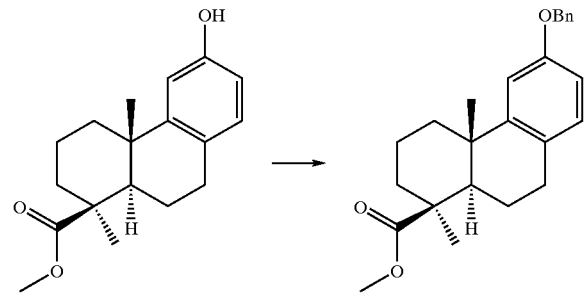

Cesium carbonate (2.74 grams) was added to a solution of methyl (4β,5α)-12-hydroxypodocarpa-8,11,13-trien-16-oate (2.2 grams) in DMF (30.0 mL), followed by benzyl bromide (0.96 mL). This mixture was stirred for 1 hour. A further portion of cesium carbonate (0.27 grams) and benzyl bromide (0.095 mL) were added. After a further half hour the reaction was partitioned in ethyl acetate and water. The organic phase was separated and washed with brine. The organic phase was dried over magnesium sulfate and the solvent was evaporated to give the titled compound (3.0 grams).

Selected signals $^1$H NMR (CDCl$_3$) δ 7.46–7.31 (m, 5H), 6.98 (d, 1H), 6.71 (d, 1H), 6.76 (d, 1H), 5.13 (s, 2H), 3.68 (s, 3H) 2.88 (dd, 1H), 2.76 (m, 1H) ppm.

STEP C: Preparation of (4β,5α)-12-(Benzyloxy)podocarpa-8,11,13-trien-16-oic acid.

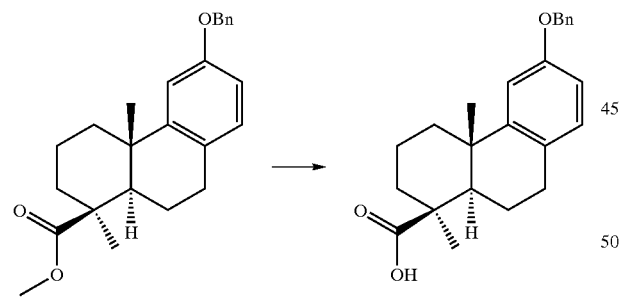

Potassium t-butoxide (8.51 grams) was added to a solution of methyl (4β,5α)-12-(benzyloxy)podocarpa-8,11,13-trien-16-oate (2.87 grams) in DMSO (50.0 mL) at 100° C. This mixture was stirred for 1 hour, was cooled, followed by partitioning between ethyl acetate and water. The organic phase was separated and washed with brine. The organic phase was dried over magnesium sulfate and the solvent was evaporated. The resulting solid was chromatographed on silica gel using ethyl acetate and hexane (1:9) to give the titled compound (2.3 grams).

Selected signals $^1$H NMR (CDCl$_3$) δ 7.46–7.31 (m, 5H), 6.98 (d, 1H), 6.70 (d, 1H), 6.76 (d, 1H), 5.13 (s, 2H), 2.88 (dd, 1H), 2.76 (m, 1H) ppm.

STEP D: Preparation of (1-phenylcyclobutyl)methylamine.

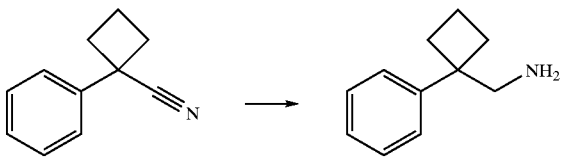

1-Phenylcyclobutanecarbonitrile (0.971 mL) was treated with lithium aluminium hydride (6.36 mL, 1.0 M in THF) in dry ether (8.0 ml) at 0° C. This mixture was then warmed to room temperature and stirred for 20 min. This mixture was then quenched with consecutive portions of H$_2$O (0.5 ml), 1N NaOH (1.0 ml), and again H$_2$O (1.0 ml). A white precipitate was formed and the mixture was filtered through Celite. The filtrate was dried over magnesium sulfate and the solvent was evaporated to give the titled compound (0.855 g).

Selected signals $^1$H NMR (CDCl$_3$) δ 7.38–7.11 (m, 5H), 2.98 (s, 2H), ppm. MS: m/z=162 (M+H).

STEP E: Preparation of (4β,5α)-12-(Benzyloxy)-N-[(1-phenylcyclobutyl)methyl]podocarpa-8,11,13-trien-16-amide.

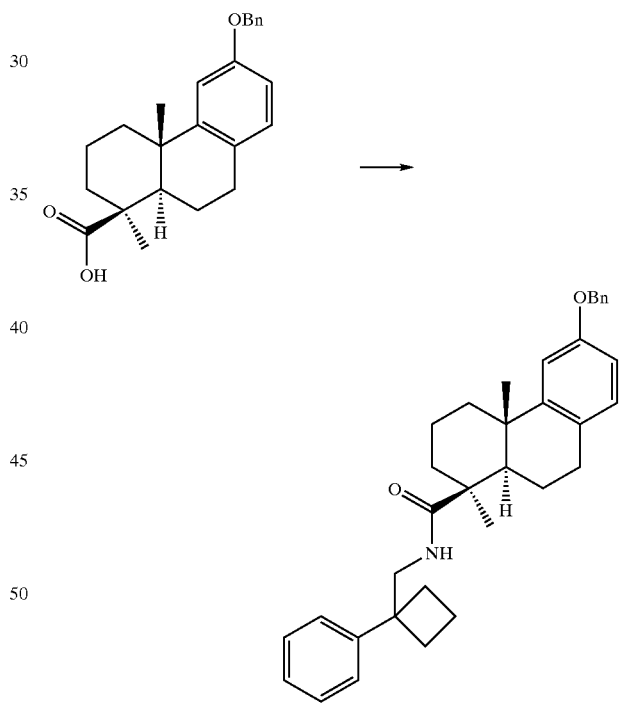

(4β,5α)-12-(Benzyloxy)podocarpa-8,11,13-trien-16-oic acid (0.060 grams) was treated with 1-(3-dimethylaminopropyl)-3-ethylcarbodiimide hydrochloride (35 mg) and 1-hydroxybenzotriazole hydrate (32 mg) in methylene chloride (1 mL). After 30 minutes the solvents were removed by evaporation. (1-phenylcyclobutyl)methylamine (0.077 grams) and DMF (1 ml) were added, and the mixture stirred for 16 hours. The solvent was mainly removed by evaporation and the resulting syrup was chromatographed on silica gel using ethyl acetate and hexane (1:5) to give the titled compound (0.037 grams).

Selected signals ¹H NMR (CDCl₃) δ 7.47–7.16 (m, 10H), 6.96 (d, 1H), 6.88 (d, 1H), 6.75 (d, 1H), 5.33 (m, 1H) 5.03 (s, 2H) 3.71 (dd, 1H), 3.60 (dd, 1H) 2.80 (dd, 1H) 2.69 (m, 1H), ppm.

MS: m/z=508 (M+H).

STEP F: Preparation of (4β,5α)-12-Hydroxy-N-[(1-phenylcyclobutyl)methyl]podocarpa-8,11,13-trien-16-amide.

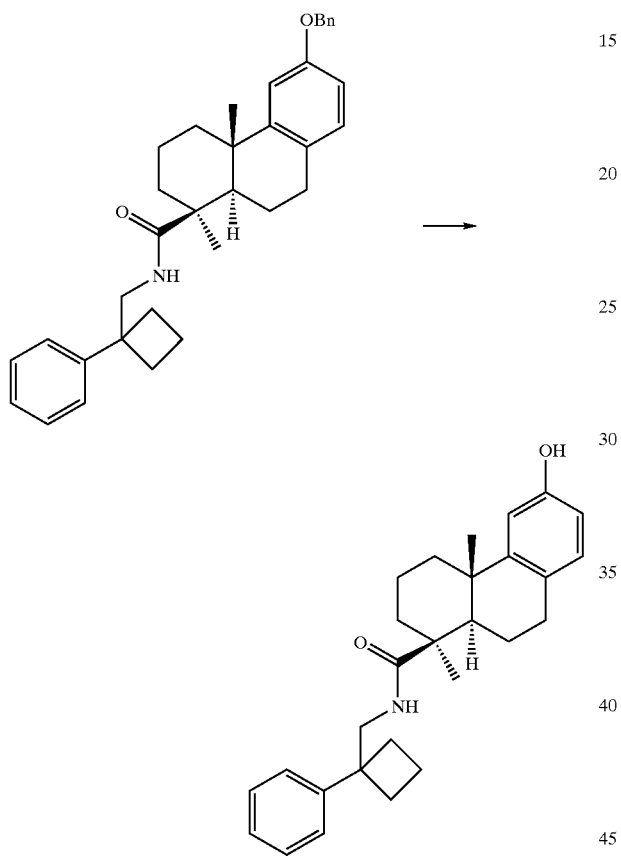

Palladium on carbon (0.015 grams) was added to a solution of (4β,5α)-12-(benzyloxy)-N-[(1-phenylcyclobutyl)methyl]podocarpa-8,11,13-trien-16-amide (0.023 grams) in ethyl acetate (4 mL) and acetic acid (0.8 mL). The mixture was reacted under 50 psi of hydrogen for 16 hours. Filtration of the reaction mixture through Celite™ was followed by evaporation of the solvent. The resulting solid was chromatographed on silica gel using ethyl acetate and hexane (1:5) to give the titled compound (0.013 grams).

Selected signals ¹H NMR (CDCl₃) δ 7.40–7.18 (m, 5H), 6.88 (d, 1H), 6.74 (d, 1H), 6.62 (d, 1H), 5.35 (m, 1H), 3.70 (dd, 1H), 3.58 (dd, 1H) 2.75 (dd, 1H), 2.66 (m, 1H) ppm.

MS: m/z=418 (M+H).

EXAMPLE 5

Preparation of (4β,5α)-12-(Acetyloxy)-N-[2-(4-Fluorophenyl)ethyl]podocarpa-8,11,13-trien-16-amide

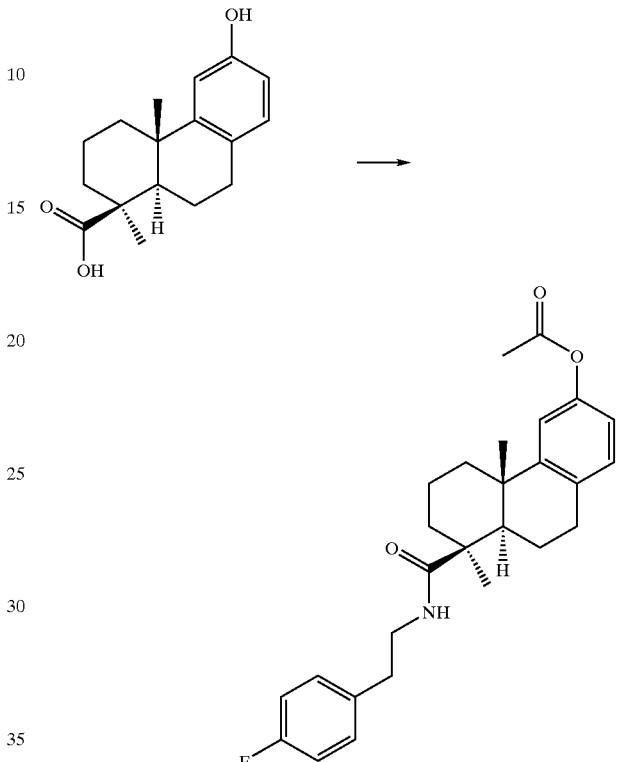

To a solution of 100 mg (0.36 mmole) of (4β,5α)-12-hydroxypodocarpa-8,11,13-trien-16-oic acid in 1 mL pyridine, was added 200 μL of acetic anhydride. The reaction mixture was stirred at room temperature for 2 hours and worked up. To a solution of 95 mg (0.30 mmole) of 12-acetoxy-podocarpic acid in 0.5 ml toluene, was added 175 μl (2 mmole) of oxalyl chloride. The reaction mixture was stirred for 1 hour at room temperature and then refluxed until the gas evolution was complete. The reaction mixture was concentrated to dryness to give acid chloride (0.28 mmole) which was dissolved in 1 μmL pyridine and stirred for a few minutes. To the stirred solution was added 84 μL (0.6 mmole) of 4-fluorophenethylamine and the reaction was continued at 30° C. overnight. The product was diluted with ethyl acetate and sequentially washed with dilute HCl (pH=1.5), 25% NaCl solution and dried over sodium sulfate. The ethyl acetate extract was dried under vacuum and the residue was purified by reverse-phase HPLC on a Zorbax C8 column with a 25 min gradient of 25 to 95% gradient of H₂O: CH₃CN as eluting solvent at a flow rate of 1 mL/min.

¹H NMR (CDCl₃) δ: 7.20 (2H, m), 7.04 (2H, m), 6.94 (1H, d, J=8.2 Hz), 6.75 (1H, d, J=2.8 Hz), 6.61 (1H, dd, J=2.8, 8.2 Hz), 5.67 (1H, t, J=5.5 Hz), 3.52 (2H, m), 2.84 (2H, t, J=7.3 Hz), 2.73 (1H, m), 2.14 (3H, m), 1.92 (2H, m), 1.62 (1H, m), 1.51 (1H, dd, J=11, 1.2 Hz), 1.40 (1H, m), 1.23 (3H, s), 1.17 (1H, dt, J=14, 4.1 Hz), 1.08 (3H, s).

EXAMPLE 6

Preparation of (4β,5α)-12-Hydroxy-N-{[1-(3-methoxyphenyl)cyclohexyl]methyl}podocarpa-8,11,13-trien-16-amide STEP A: Preparation of 1-(3-Methoxyphenyl)cyclohexanecarbonitrile.

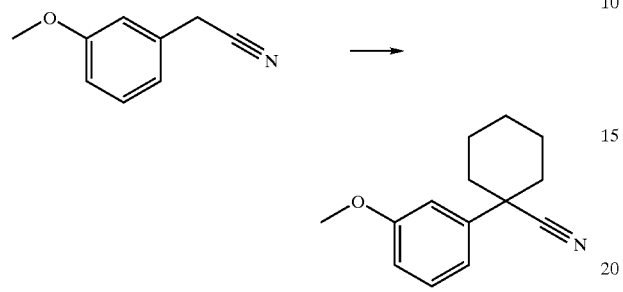

(3-Methoxyphenyl)acetonitrile (0.52 grams) was added to a solution of sodium hydride (0.212 grams) in DMSO (10 mL) at 0° C. The mixture was warmed to room temperature over 30 minutes. 1,5-Dibromopentane (0.722 mL) was added dropwise as a solution in DMSO (5 mL). This mixture was stirred for 16 hours, then partitioned between ethyl acetate and water. The organic phase was separated and washed with brine. The organic phase was dried over magnesium sulfate and the solvent was evaporated. The resulting solid was chromatographed on silica gel using ethyl acetate and hexane (3:97) to give the titled compound (0.42 grams).

$^1$H NMR (CDCl$_3$) δ 7.32 (m, 1H), 7.09 (m, 1H), 7.05 (m, 1H), 6.86 (dd, 1H), 3.83 (s, 3H), 2.16 (m, 2H), 1.82 (m, 7H), 1.30 (m, 1H) ppm.

STEP B: Preparation of [1-(3-methoxyphenyl)cyclohexyl]methylamine.

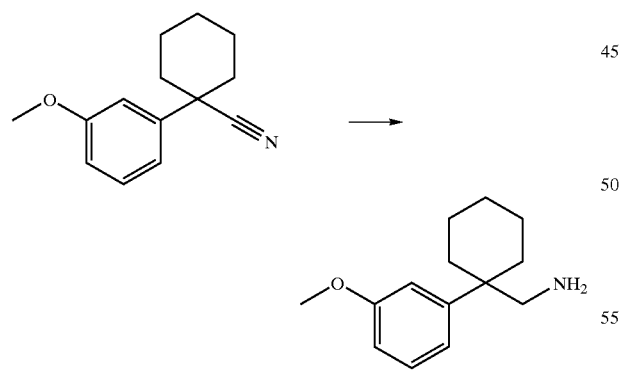

1-(3-methoxyphenyl)cyclohexanecarbonitrile (0.42 grams) was reduced according to the procedure described in Example 4, Step D to give the title compound (0.41 grams).

Selected signals $^1$H NMR (CDCl$_3$) δ 7.26 (m, 1H), 6.92 (m, 2H), 6.75 (m, 1H), 3.80 (s, 3H), 2.62 (s, 2H), 2.10 (m, 2H), 1.5 (m, 8H), 0.8 (brs, 2H) ppm.

MS: m/z=220 (M+H).

STEP C: Preparation of (4β,5α)-12-(Benzyloxy)-N-{[1-(3-methoxyphenyl)cyclohexyl]methyl}podocarpa-8,11,13-trien-16-amide.

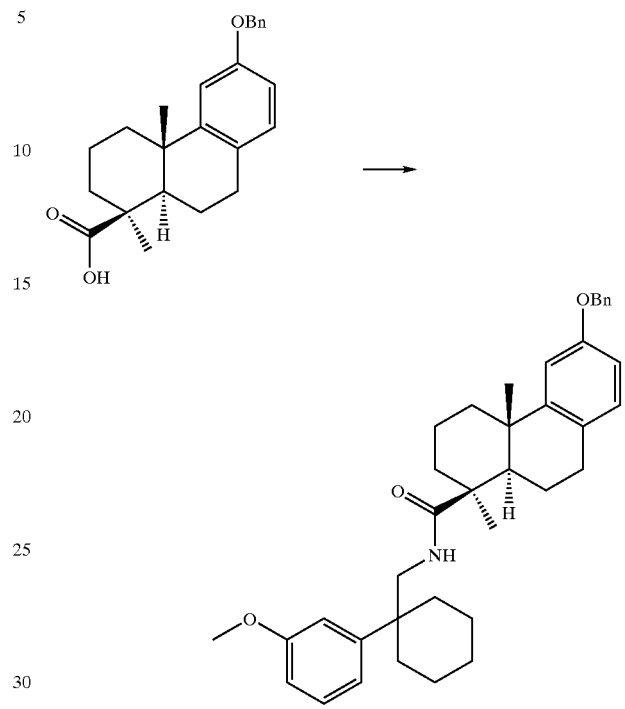

(4β,5α)-12-(Benzyloxy)podocarpa-8,11,13-trien-16-oic acid (0.048 grams) was coupled to [1-(3-methoxyphenyl)cyclohexyl]methylamine (0.087 grams) according to the procedure described in Example 4, Step E to give the title compound (0.43 grams).

Selected signals $^1$H NMR (CDCl$_3$) δ 7.46–7.32 (m, 5H), 7.20–6.74 (m, 7H), 5.19 (m, 1H), 5.02 (s, 2H), 3.82 (s, 3H), 3.46 (dd, 1H), 3.32 (dd, 1H), 2.77 (dd, 1H), 2.67 (m, 1H) ppm.

MS: m/z=566 (M+H).

STEP D: Preparation of (4β,5α)-12-Hydroxy-N-{[1-(3-methoxyphenyl)cyclohexyl]methyl}podocarpa-8,11,13-trien-16-amide.

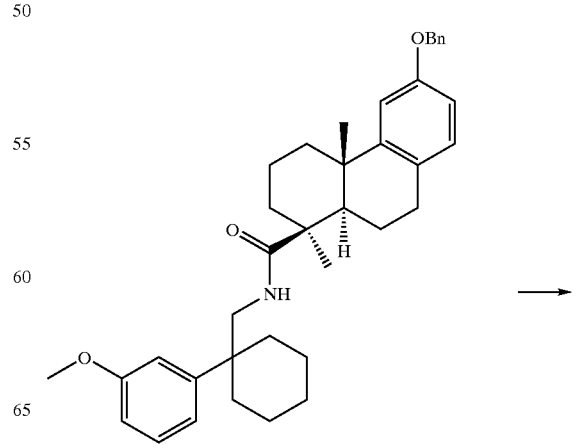

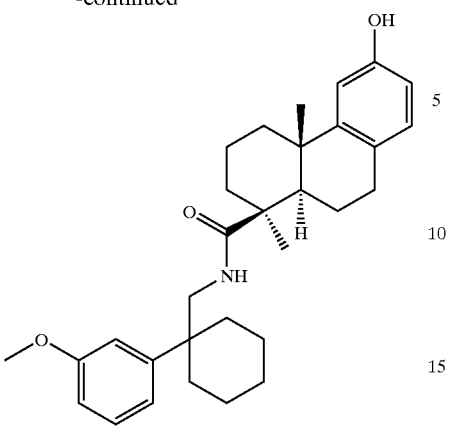

(4β,5α)-12-(Benzyloxy)-N-{[1-(3methoxyphenyl)cyclohexyl]methyl}podocarpa-8,11,13-trien-16-amide (32 mg) was reacted according to the according to the procedure described for Example 4 Step F, to give the titled compound (25 mg).

Selected signals ¹H NMR (CDCl₃) δ 7.38–7.18 (m, 2H), 7.01–6.62 (m, 5H), 5.22 (m, 1H), 3.82 (s, 3H), 3.45 (dd, 1H), 3.34 (dd, 1H), 2.74 (dd, 1H), 2.64 (m, 1H) ppm.

MS: m/z=432 (M+H).

EXAMPLE 7

Preparation of (4β,5α)-12-Hydroxy-N-{[1-(4-methoxyphenyl)cyclohexyl]methyl}podocarpa-8,11,13-trien-16-amide

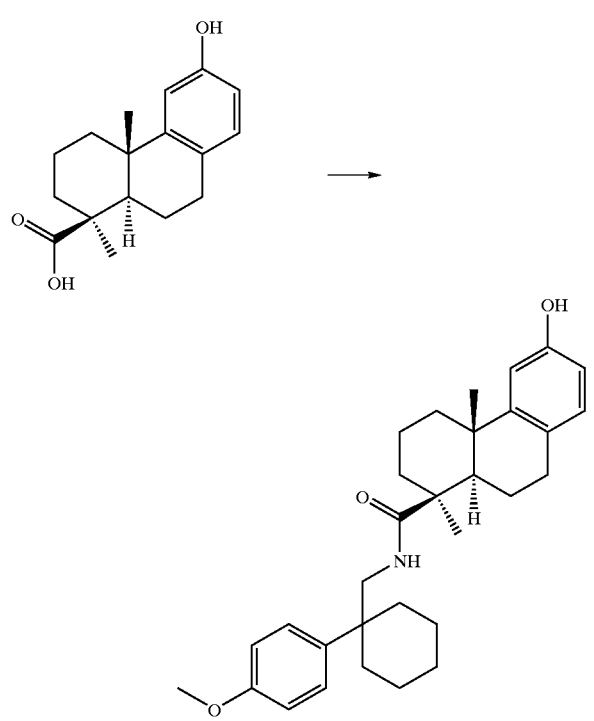

(4-Methoxyphenyl)cyclohexanecarbonitrile (1.00 grams) was treated according to the procedures described in Example 4 Steps D to F, to give the title compound (0.007 grams).

Selected signals ¹H NMR (CDCl₃) δ 7.31 (m, 2H), 6.95 (m, 2H), 6.88 (d, 1H), 6.62 (m, 1H), 5.18 (m, 1H), 3.82 (s, 3H), 3.45 (dd, 1H), 3.30 (dd, 1H), 2.75 (dd, 1H), 2.65 (m, 1H) ppm.

MS: m/z=476 (M+H).

EXAMPLE 8

Preparation of (4β,5α)-12-Hydroxypodocarpa-8,11,13-trien-16-yl (4β,5α)-12-hydroxypodocarpa-8,11,13-trien-16-oate STEP A: Preparation of (4β,5α)-12-(Benzyloxy)podocarpa-8,11,13-trien-16-ol.

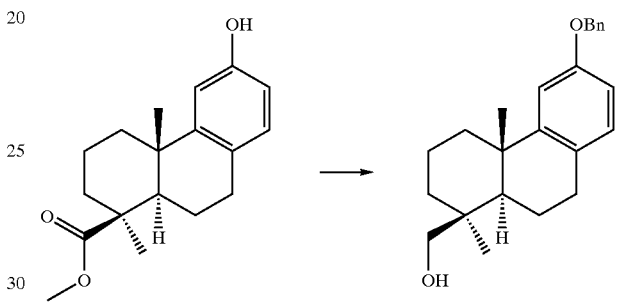

A solution of methyl (4β,5α)-12-(benzyloxy)podocarpa-8,11,13-trien-16-oate (2.06 grams) in tetrahydrofuran (300 mL) was treated with lithium aluminium hydride in tetrahydrofuran (100 mL, 1 M). This mixture was refluxed for 5 hours, then partitioned in ethyl acetate and water. The organic phase was separated and washed with brine. The organic phase was dried over magnesium sulfate and the and the solvent was evaporated. The resulting solid was chromatographed on silica gel using ethyl acetate and hexane (1:4) to give the titled compound (1.7 grams).

Selected signals ¹H NMR (CDCl₃) δ 7.48–7.30 (m, 5H), 6.97 (d, 1H), 6.90 (d, 1H), 6.75 (dd, 1H), 5.20 (s, 2H), 3.88 (d, 1H), 3.57 (d, 1H), 2.90 (dd, 1H), 2.80 (m, 1H) ppm.

STEP B: Preparation of (4β,5α)-12-(Benzyloxy)podocarpa-8,11,13-trien-16-yl (4β,10α)-12-(benzyloxy)podocarpa-8,11,13-trien-16-oate Thionyl chloride (0.120 mL) was added to a solution of (4β,5α)-12-(benzyloxy)podocarpa-8,11,13-trien-16-oic acid (0.1 grams) in dichloroethane (2 mL). This mixture was refluxed for 30 minutes then evaporated to dryness. The resulting solid was redissolved in dichloroethane (2 mL), then (4β,5α)-12-(benzyloxy)podocarpa-8,11,13-trien-16-ol (96 mg) and pyridine (0.06 mL) were added. This mixture was heated at 90° C. for 3 hours, then evaporated to dryness. The resulting solid was chromatographed on silica gel using ethyl acetate and hexane (1:19) to give the titled compound (0.18 grams).

Selected signals ¹H NMR (CDCl₃) δ 7.48–7.30 (m, 10H), 6.98 (m, 2H), 6.90 (m, 2H), 6.78 (m, 2H), 5.20 (s, 2H), 5.15 (s, 2H), 4.24 (d, 1H), 4.02 (d, 1H), 2.90 (m, 2H), 2.80 (m, 2H) ppm.

STEP C: Preparation of (4β,5α)-12-Hydroxypodocarpa-8,11,13-trien-16-yl (4β,5α)-12-hydroxypodocarpa-8,11,13-trien-16-oate.

EXAMPLE 9

Preparation of (4β,5α)-12-(Acetyloxy)podocarpa-8,11,13-trien-16-yl (4β,5α)-12-(acetyloxy)podocarpa-8(14),9(11),12-trien-16-oate

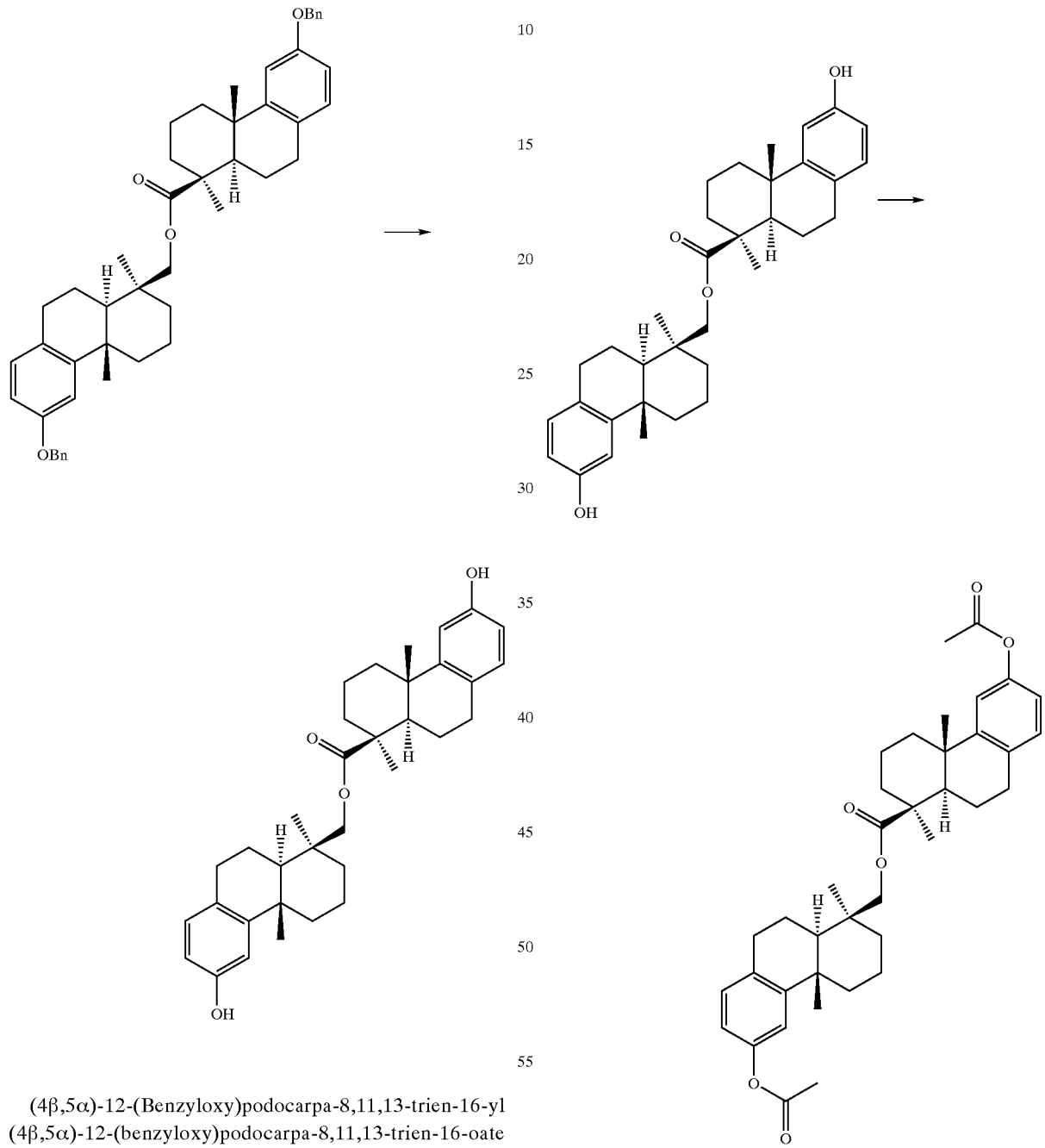

(4β,5α)-12-(Benzyloxy)podocarpa-8,11,13-trien-16-yl (4β,5α)-12-(benzyloxy)podocarpa-8,11,13-trien-16-oate (0.17 grams) was hydrogenated according to the procedure described in Example 4 Step F to give the titled compound (42 mg).

Selected signals $^1$H NMR (CDCl$_3$) δ 6.93 (m, 2H), 6.75 (m, 2H), 6.60 (m, 2H), 4.24 (d, 1H), 4.04 (d, 1H), 2.88 (m, 2H), 2.78 (m, 2H) ppm.

Acetic anhydride (0.04 mL) was added to a solution of (4β,5α)-12-(hydroxy)podocarpa-8,11,13-trien-16-yl (4β,5α)-12-(hydroxy)podocarpa-8(14),9(11),12-trien-16-oate (44 mg) in pyridine (0.5 mL). After stirring for 17 hours, the mixture was evaporated to dryness. The resulting solid was chromatographed on silica gel using ethyl acetate and hexane (1:9) to give the titled compound (29 mg).

Selected signals $^1$H NMR (CDCl$_3$) δ 7.08 (m, 2H), 6.96 (m, 2H), 6.83 (m, 2H), 4.24 (d, 1H), 4.04 (d, 1H), 2.95 (m, 2H), 2.84 (m, 2H), 2.23 (s, 3H), 2.23 (s, 3H), ppm.

EXAMPLE 10

Preparation of (4β,5α)-12-(Hydroxy)podocarpa-8,11,13-trien-16-oic anhydride

STEP A: Preparation of (4β,5α)-12-(Benzyloxy)podocarpa-8,11,13-trien-16-oic anhydride

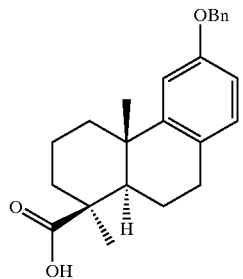

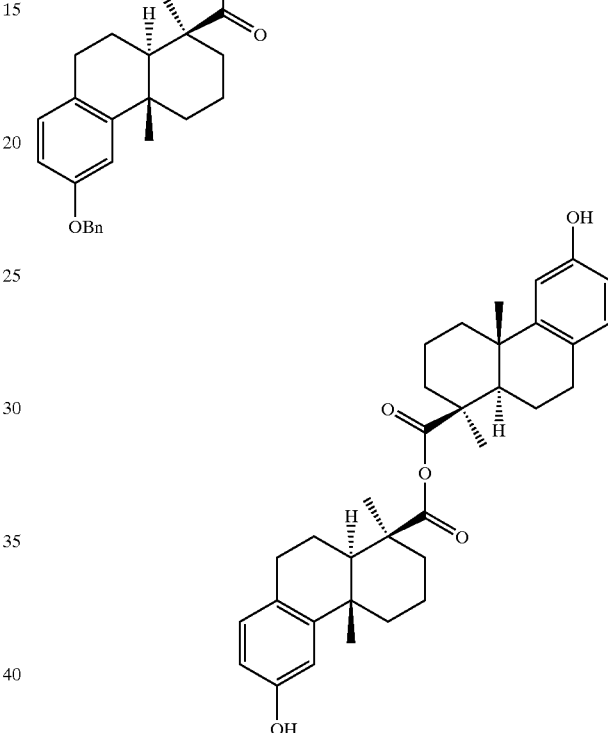

A solution of (4β,5α)-12-(benzyloxy)podocarpa-8,11,13-trien-16-oic acid (0.25 grams) in refluxing 1,2-dichloroethane (7 mL) was treated with 1-(3-dimethylaminopropyl)-3-ethylcarbodiimide hydrochloride (72 mg). This mixture was refluxed for 3 hours, then allowed to stir at room temperature overnight. The solvent was partially removed by evaporation and the resulting syrup was chromatographed on silica gel using ethyl acetate and hexane (3:97) to give the titled compound (77 mg).

Selected signals $^1$H NMR (CDCl$_3$) δ 7.45 (m, 4H), 7.40 (m, 4H), 7.34 (m, 2H), 7.00 (d, 2H), 6.91 (d, 2H), 6.78 (dd, 2H), 5.05 (s, 4H), 2.92 (dd, 2H), 2.79 (m, 2H) ppm.

STEP B: Preparation of (4β,5α)-12-(Hydroxy)podocarpa-8,11,13-trien-16-oic anhydride

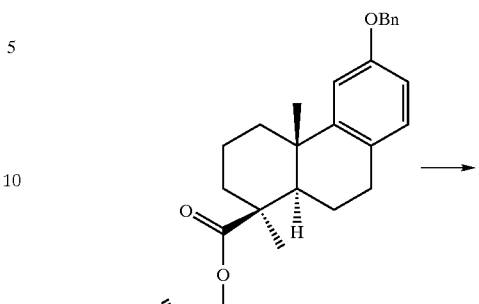

A solution of (4β,5α)-12-(benzyloxy)podocarpa-8,11,13-trien-16-oic anhydride (20 mg) in methanol was hydrogenated according to the procedure described in Example 4 step F to give the titled compound (16 mg).

Selected signals $^1$H NMR (CDCl$_3$) δ 6.94 (d, 2H), 6.77 (m, 2H), 6.67 (d, 2H), 2.90 (dd, 2H), 2.77 (m, 2H) ppm.

EXAMPLE 11

Preparation of (4β,5α)-12-Hydroxy-N-[(4β,5α)-12-hydroxy-16-oxopodocarpa-8,11,13-trien-16-yl]podocarpa-8,11,13-trien-16-amide STEP A: Preparation of (4β,5α)-12-(Benzyloxy)podocarpa-8,11,13-trien-16-amide.

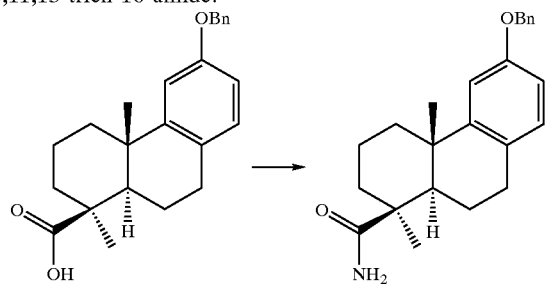

Thionyl chloride (40.47 mmoles) was added to a 1,2dichloroethane solution of (4β,5α)-12-(benzyloxy)podocarpa-8,11,13-trien-16-oic acid (6.86 mmoles) at 25° C. The reaction was heated at reflux for 0.5 h The reaction was then bubbled briefly with nitrogen and concentrated on the rotary evaporator, flushing with anhydrous THF. The crude acid chloride was then treated with 0.5M ammonia in dioxane (30 mmoles) and let stir at 25° C. for 0.5 h when TLC indicated conversion to a more polar product. The reaction was concentrated prior to partitioning between ethyl acetate and 5% aqueous sodium bicarbonate. The organic phase was separated and washed with water followed by brine. The organic phase was then dried over magnesium sulfate and the solvent was evaporated to give the crude amide. The compound was then purified on silica gel using acetone/hexanes (50:50) to give the titled compound.

Characteristic NMR Resonances; $^1$H NMR 500 MHz (CDCl$_3$); 7.34–7.46 (ArH, 5H), 6.99 (d, 1H, J=8.3 Hz), 6.92 (d, 1H, J=2.5 Hz), 6.77 (dd, 1H, J=2.5 & 8.5 Hz) 5.66 (broad s, 1H), 5.37 (broad s, 1H), 5.05 (s, 1H), 2.91 (m, 1H), 2.79 (m, 1H), 2.23 (m, 2H), 2.06 (m, 2H), 1.33 (s, 3H), 1.21 (s, 3H)

MS (ESI):(M+H)=364.4

STEP B: Preparation of (4β,5α)-12-(Benzyloxy)-N-[(4β,5α)-12-(benzyloxy)-16-oxopodocarpa-8,11,13-trien-16-yl]podocarpa-8,11,13-trien-16-amide.

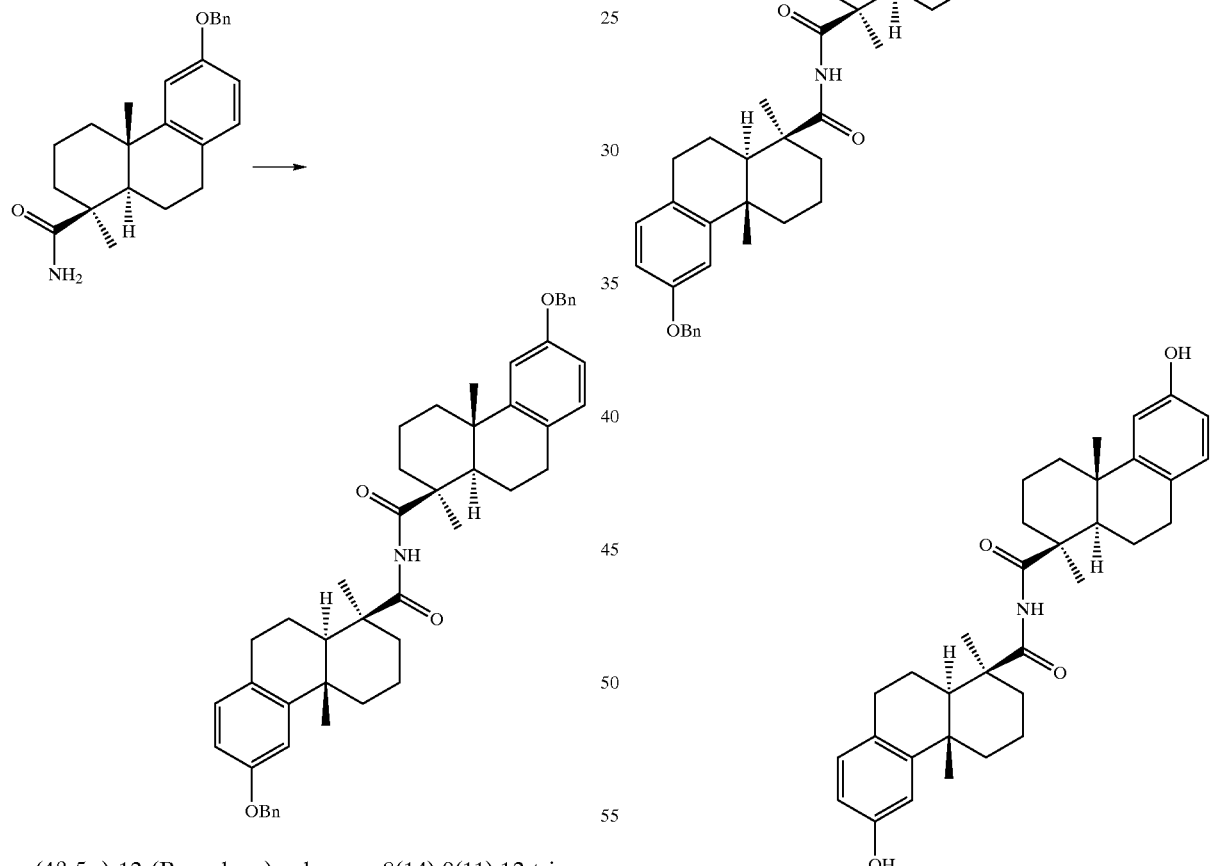

(4β,5α)-12-(Benzyloxy)podocarpa-8(14),9(11),12-trien-15-amide (2.75 mmoles) was dissolved in THF and treated with sodium bis(trimethylsilyl) amide (1.0 M in THF, 2.89 mmoles) at 0° C. This was allowed to stir for 1 h. Separately, thionyl chloride (16.2 mmoles) was added to a 1,2 dichloroethane solution of (4β,5α)-12-(benzyloxy)podocarpa-8,11,13-trien-16-oic acid (2.75 mmoles) at 25° C. The reaction was heated at reflux for 0.5 h The reaction was then bubbled briefly with nitrogen and concentrated on the rotary evaporator, flushing with anhydrous THF. A THF solution of this mixture was added drop-wise via an addition funnel at 0° C. to the first mixture. The reaction was then allowed to warm to 25° C. and monitored by TLC. After 2 h, the reaction was complete and work-up was initiated. The reaction mixture was poured into saturated ammonium chloride and extracted with ethyl acetate. The organic phase was separated and washed with water followed by brine. The organic phase was then dried over magnesium sulfate and the solvent was evaporated to give the crude imide. The compound was then purified on silica gel using ethyl acetate/hexanes (40:60) to give the titled compound.

Characteristic NMR Resonances; $^1$H NMR 500 MHz (CDCl$_3$); 8.18 (s, 1H), 7.34–7.45 (ArH, 10H), 7.00 (d, 2H, J=8.5 Hz), 6.90 (d, 2H, J=2.6 Hz), 6.78 (dd, 2H, J=2.5 & 8.5 Hz), 5.04 (s, 4H), 2.97 (m, 2H), 2.85 (m, 2H), 2.27 (m, 4H), 2.08 (m, 4H), 1.34 (s, 6H), 1.17 (s, 6H)

STEP C: Preparation of (4β,5α)-12-Hydroxy-N-[(4β,5α)-12-hydroxy-16-oxopodocarpa-8,11,13-trien-16-yl]podocarpa-8(14),9(11),12-trien-16-amide.

(4β,5α)-12-(Benzyloxy)-N-[(4β,5α)-12-(benzyloxy)-16-oxopodocarpa-8,11,13-trien-16-yl]podocarpa-8(14),9(11),12-trien-16-amide (1.13 mmoles) was dissolved in ethyl acetate and charged with palladium hydroxide on carbon catalyst (800 mg). This suspension was then stirred under hydrogen atmosphere (balloon) for 2 hours. HPLC analysis showed conversion to more polar product. The reaction was purged with nitrogen and filtered through a 2 inch pad of Celite™, rinsing with ethyl acetate. The filtrate was concentrated and foamed with methyl t-butyl ether to give the titled compound.

Characteristic NMR Resonances; $^1$H NMR 500 MHz (CD$_3$OD); 8.37 (s, 1H), 6.86 (d, 2H, J=8.3 Hz), 6.70 (d, 2H, J=2.3 Hz), 6.53 (dd, 2H, J=2.3 & 8.3 Hz), 2.89 (m, 2H), 2.77 (m, 2H), 2.32 (m, 2H), 2.26 (m, 4H), 2.03 (m, 4H), 1.68 (m, 4H), 1.35 (s, 6H), 1.11 (s, 6H)

MS (ESI): (M+H)=530.4

EXAMPLE 12

Preparation of N-[(4β,5α)-12-Hydroxy-16-oxopodocarpa-8,11,13-trien-16-yl]-1-phenylcyclohexanecarboxamide STEP A: Preparation of N-[(4β,5α)-12-(Benzyloxy)-16-oxopodocarpa-8,11,13-trien-16-yl]-1-phenylcyclohexanecarboxamide.

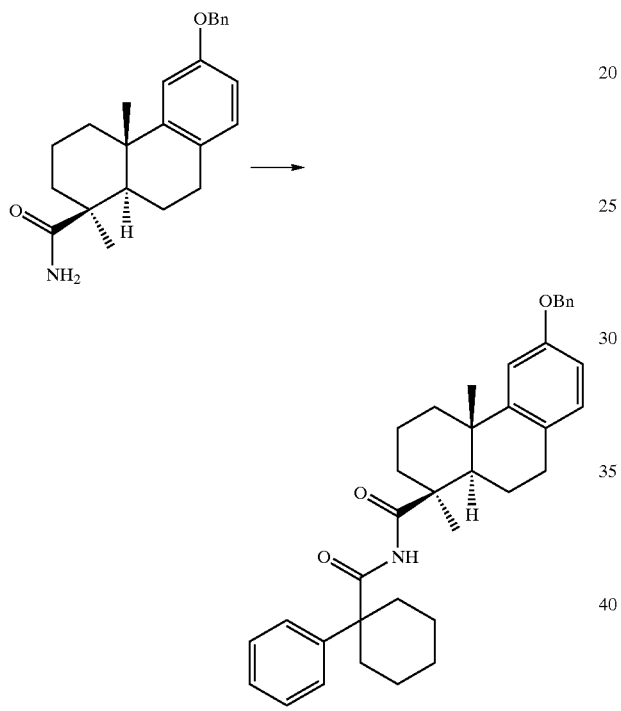

(4β,5α)-12-benzyloxy-16-oxopodocarpa-8(14),9(11),12-trien-16-amide (0.25 mmoles) was dissolved in THF and treated with sodium bis(trimethylsilyl) amide (1.0 M in THF, 2.89 mmoles) at 0° C. This was allowed to stir for 1 h. Separately, thionyl chloride (16.2 mmoles) was added to a 1,2-dichloroethane solution of 1-phenyl cyclohexane carboxylic acid (0.25 mmoles) at 25° C. The reaction was heated at reflux for 0.5 h. The reaction was then bubbled briefly with nitrogen and concentrated on the rotary evaporator, flushing with anhydrous THF. A THF solution of this mixture was added drop-wise via an addition funnel at 0° C. to the first mixture. The reaction was then allowed to warm to 25° C. and monitored by TLC. After 18 h, the reaction was complete and work-up was initiated. The reaction mixture was poured into saturated ammonium chloride and extracted with ethyl acetate. The organic phase was separated and washed with water followed by brine. The organic phase was then dried over magnesium sulfate and the solvent was evaporated to give the crude imide. The compound was then purified on silica gel using ethyl acetate/hexanes (30:70) with 0.1% acetic acid to give the titled compound.

Characteristic NMR Resonances; $^1$H NMR 500 MHz (CDCl$_3$); 7.70 (s, 1H), 7.34–7.46 (ArH, 10H), 6.94 (d, 1H, J=8.2 Hz), 6.83 (d, 1H, J=2.5 Hz), 6.75 (dd, 1H, J=2.5 & 8.4 Hz), 0.99 (s, 3H), 0.92 (s, 3H)

STEP B: Preparation of N-[(4β,5α)-12-Hydroxy-16-oxopodocarpa-8,11,13-trien-16-yl]-1-phenylcyclohexanecarboxamide.

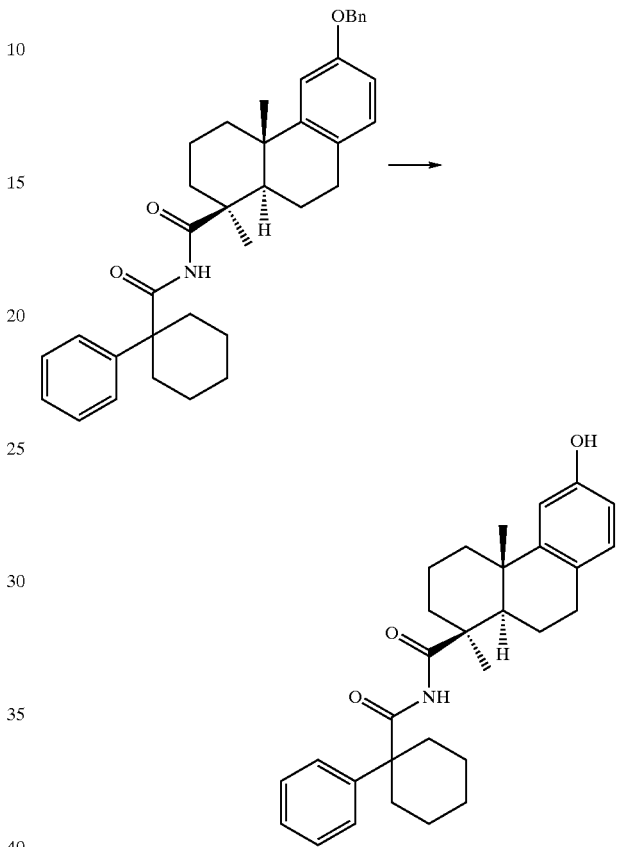

N-[(4β,5α)-12-(Benzyloxy)-16-oxopodocarpa-8,11,13-trien-16-yl]-1-phenylcyclohexanecarboxamide was hydrogenated according to the procedure described in Example 4 Step F.

MS (ESI): (M+H)=460.3

EXAMPLE 13

Preparation of 1,3-bis[(4β,5α)-12-(Hydroxy)-16-oxopodocarpa-8,11,13-trien-16-yl]propane-1,3-dione STEP A: Preparation of (4β,5α)-12-(Benzyloxy)podocarpa-8,11,13-trien-16-al.

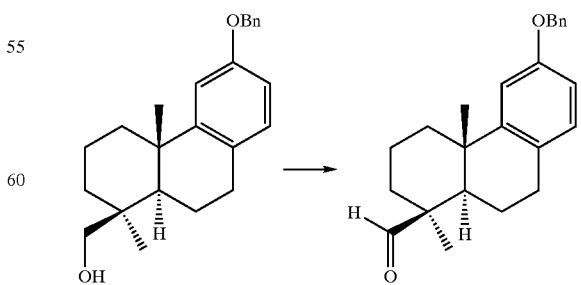

A methylene chloride solution of (4β,5α)-12-(benzyloxy)podocarpa-8,11,13-trien-16-ol (0.82 mmoles) and 4-methylmorpholine N-oxide (0.98 mmoles) was treated with tetrapropylammonium perruthenate (0.16 mmoles) at 25° C. TLC analysis at 10 min. showed conversion to product. The compound was then purified on silica gel using ethyl acetate/hexanes (20:80) to give the titled compound.

Characteristic NMR Resonances; $^1$H NMR 500 MHz (CDCl$_3$); 9.86 (d, 1H, J=0.9 Hz) 7.34–7.46 (ArH, 5H), 7.00 (d, 1H, J=8.5 Hz), 6.91 (d, 1H, J=2.5 Hz), 6.77 (dd, 1H, J=2.5 & 8.5 Hz), 5.05 (s, 1H), 2.96 (m, 1H), 2.85 (m, 1H), 2.25 (m, 4H), 2.03 (m, 2H), 1.14 (s, 3H), 1.08 (s, 3H)

STEP B: Preparation of (4β,5α)-12-(Benzyloxy)-16-hydroxy-16-homopodocarpa-8,11,13-triene.

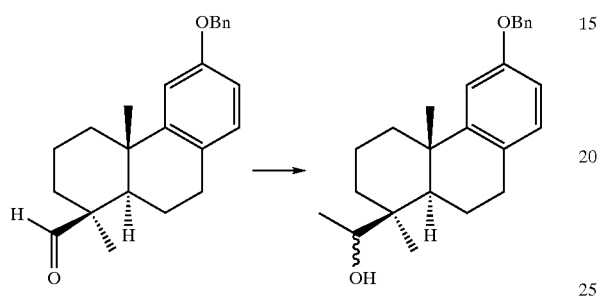

A THF solution of (4β,5α)-12-(benzyloxy)podocarpa-8,11,13-trien-16-al (0.75 mmoles) was treated with methyl lithium (1.4 M in diethylether, 1.13 mmoles) under nitrogen at −78° C. TLC analysis showed conversion to more polar product. The reaction was then poured into saturated ammonium chloride and extracted with ethyl acetate. The organic phase was separated and washed with water followed by brine. The organic phase was then dried over magnesium sulfate and the solvent was evaporated to give the crude alcohol. This was then used in next step without purification.

MS (ESI): (M+CH$_3$CN+Na)=428.3

STEP C: Preparation of (4β,5α)-12-(Benzyloxy)-16-oxo-16-homopodocarpa-8,11,13-triene.

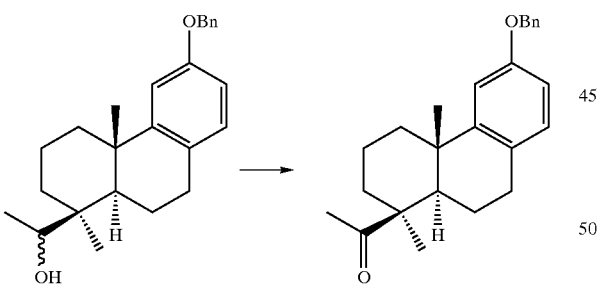

A methylene chloride solution of the (4β,5α)-12-(Benzyloxy)-16-hydroxy-16-homopodocarpa-8,11,13-triene (0.82 mmoles) and 4-methylmorpholine N-oxide (Aldrich, 0.98 mmoles) was treated with tetrapropylammonium perruthenate (Aldrich, 0.16 mmoles) at 25° C. TLC analysis at 10 min. showed conversion to product. The compound was then purified on silica gel using ethyl acetate/hexanes (20:80) to give the titled compound.

Characteristic NMR Resonances; $^1$H NMR 500 MHz (CDCl$_3$); 7.32–7.46 (ArH, 5H), 6.99 (d, 1H, J=8.2 Hz), 6.90 (d, 1H, J=2.7 Hz), 6.77 (dd, 1H, J=2.7 & 8.4 Hz), 5.04 (s, 1H), 2.91 (m, 1H), 2.77 (m, 1H), 2.24 (s, 3H), 1.23 (s, 3H), 1.06 (s, 3H)

STEP D: Preparation of 1,1-bis[(4β,5α)-12-(Benzyloxy)-16-oxopodocarpa-8,11,13-trien-16-yl]}methane.

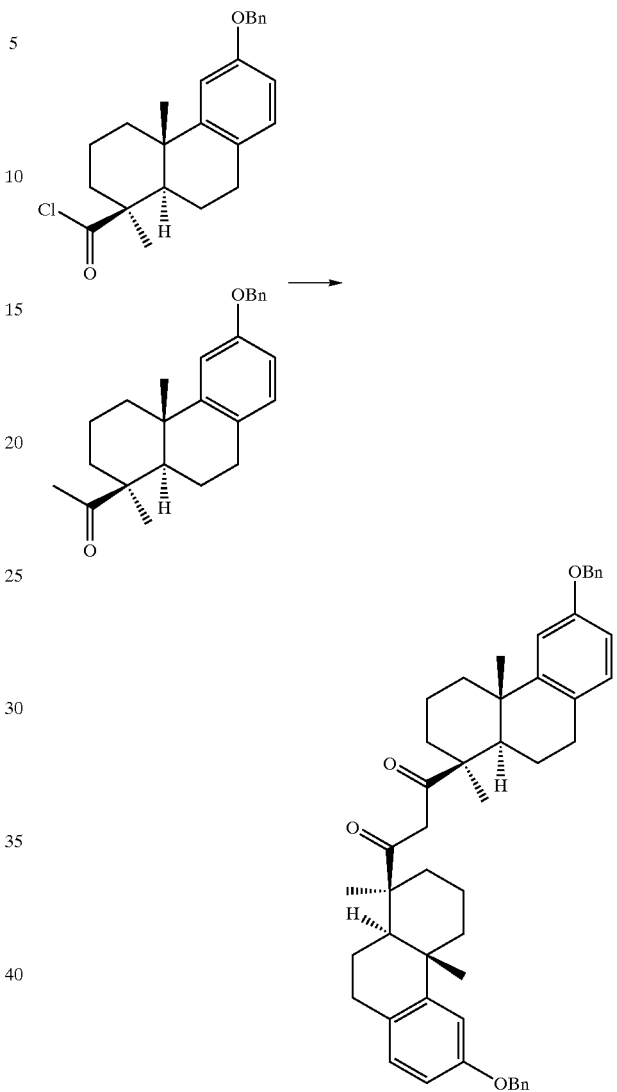

(4β,5α)-12-(Benzyloxy)-16-oxo-16-homopodocarpa-8,11,13-triene (0.30 mmoles) was dissolved in THF and treated with sodium bis(trimethylsilyl) amide (1.0 M in THF, 0.32 mmoles) at −40° C. Separately, thionyl chloride (1.76 mmoles) was added to a 1,2 dichloroethane solution of (4β,5α)-12-(benzyloxy)podocarpa-8,11,13-trien-16-oic acid (0.30 mmoles) at 25° C. The reaction was heated at reflux for 0.5 h The reaction was then bubbled briefly with nitrogen and concentrated on the rotary evaporator, flushing with anhydrous THF. A THF solution of this mixture was added drop-wise via an addition funnel at 0° C. to the first mixture. The reaction was then allowed to warm to 25° C. and monitored by TLC. After 0.5 h, the reaction was complete and work-up was initiated. The reaction mixture was poured into saturated ammonium chloride and extracted with ethyl acetate. The organic phase was separated and washed with water followed by brine. The organic phase was then dried over magnesium sulfate and the solvent was evaporated to give the crude diketone. The compound was then purified on silica gel using ethyl acetate/hexanes (10:90) to give the titled compound.

Characteristic NMR Resonances; ¹H NMR 500 MHz (CDCl₃); 16.69 (s, enol 1H), 7.35–7.47 (ArH, 10H), 7.01 (d, 2H, J=8.5 Hz), 6.91 (d, 2H, J=2.5 Hz), 6.79 (dd, 2H, J=2.5 & 8.5 Hz), 6.00 (s, 1H), 5.06 (s, 4H), 2.93 (m, 2H), 2.79 (m, 2H), 2.32 (m, 2H), 2.24 (m, 4H), 1.32 (s, 6H), 1.10 (s, 6H)

STEP E: Preparation of 1,1-bis[(4β,5α)-12-(hydroxy)-16-oxopodocarpa-8,11,13-trien-16-yl]}methane.

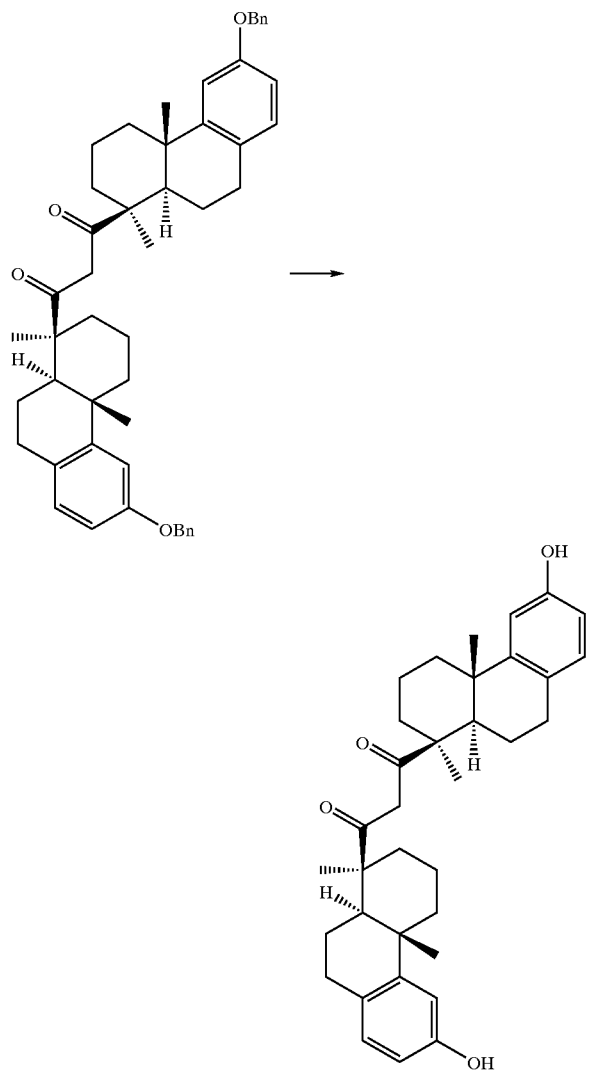

1,1-bis[(4β,5α)-12-(Benzyloxy)-16-oxopodocarpa-8,11,13-trien-16-yl]}methane (0.095 mmoles) was dissolved in ethyl acetate and charged with palladium hydroxide on carbon catalyst (Aldrich, 60 mg). This suspension was then stirred under hydrogen atmosphere (balloon) for 2 h. HPLC analysis showed conversion to more polar product. The reaction was purged with nitrogen and filtered through a 0.45µ Millex™ filter, rinsing with ethyl acetate. The filtrate was concentrated and foamed with methyl t-butyl ether to give the titled compound.

Characteristic NMR Resonances; ¹H NMR 500 MHz (CDCl₃); 16.69 (s, enol 1H), 6.94 (d, 2H, J=8.2 Hz), 6.73 (d, 2H, J=2.5 Hz), 6.61 (dd, 2H, J=2.5 & 8.2 Hz), 5.97 (s, 1H), 2.81 (m, 2H), 2.74 (m, 2H), 2.28 (m, 2H), 2.21 (m, 4H), 1.30 (s, 6H), 1.07 (s, 6H)

MS (ESI): (M+H)=529.3

EXAMPLE 14

Preparation of (4β,5α)-N-(1-Adamantylmethyl)-12-hydroxypodocarpa-8,11,13-trien-16-amide STEP A: Preparation of (4β,5α)-16-(1H-1,2,3-Benzotriazol-1-yloxy)-16-oxopodocarpa-8,11,13-trien-12-ol.

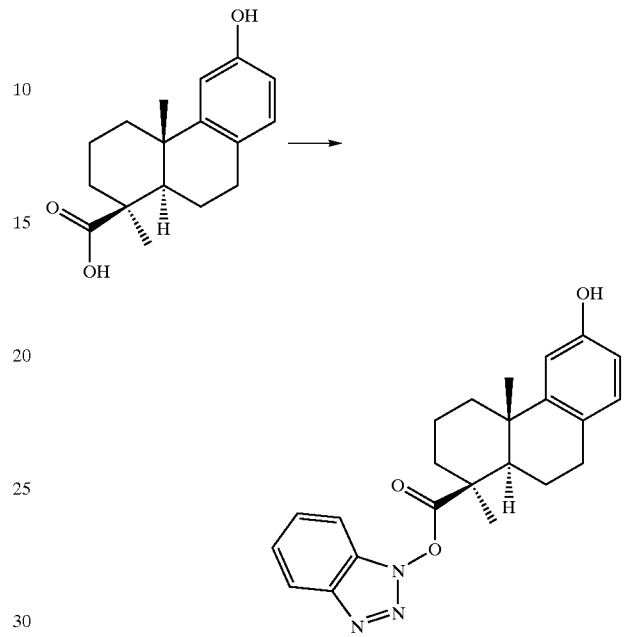

(4β,5α)-12-Hydroxypodocarpa-8,11,13-trien-16-oic acid (2.0 g, 7.2 mmol) and benzotriazol-1-yloxytris(dimethylamino)phosphonium hexafluorophosphate (3.2 g, 7.2 mmol) was added to 50 ml DMF. The mixture was stirred for 10 minutes. Diisopropylethylamine (2 mL, 11.5 mmol) was added and the solution was stirred for 8 hours at ambient temperature. The mixture was concentrated to solid by removing the organic solvent under reduced pressure. The solid was dissolved in 50 mL ethyl acetate and washed with water (2×100 mL) and brine (50 mL). The product solution was dried over magnesium sulfate and filtered. Evaporation of solvent gave 2.9 g of the titled compound.

¹HNMR (DMSO-d₆) δ: 9.01 (1H, s), 8.15 (1H, d, J=8.5 Hz), 7.69–7.64 (2H, m), 7.54–7.51 (1H, m), 6.83 (1H, d, J=8.0 Hz), 6.71 (1H, brs), 6.54–6.52 (1H, m), 3.50 (1H, m), 2.81–2.51 (2H, m), 2.22–1.82 (12H, m), 1.64 (3H, s), 1.45–1.36 (1H, m) 1.22 (3H, s).

ESIMS (m/z) 392 (M+H)⁺.

STEP B: Preparation of (4β,5α)-N-(1-Adamantylmethyl)-12-hydroxypodocarpa-8,11,13-trien-16-amide

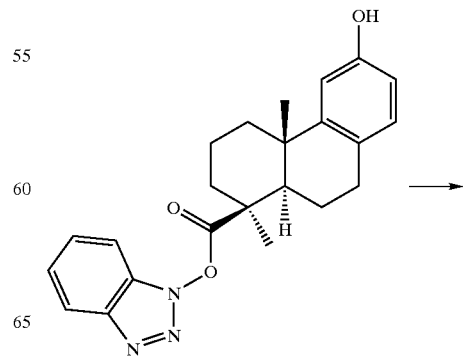

-continued

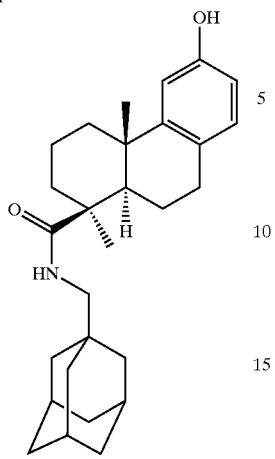

To a solution of (4β,5α)-16-(1H-1,2,3-benzotriazol-1-yloxy)-16-oxopodocarpa-8,11,13-trien-12-ol (0.5 g, 1.3 mmol) in DMF (3 mL) was added 1-adamantanemethyl-amine (0.21 g, 1.3 mmol). The resulting solution was heated to 70° C. under nitrogen for 15 hours. After removing all organic solvent, the crude product was purified by preparative HPLC (45 min gradient of acetonitrile/water 25–95% at a flow rate of 15 mL/min Zorbax RX C-8, 21.2 mm×25 cm), 200 mg of the titled compound was obtained as a white solid (36%).

$^1$R (CDCl$_3$) δ: 6.92 (1H, d, J=8.0 Hz), 6.77 (1H, d, J=2.4 Hz), 6.62 (1H, dd, J=8.0, 2.4 Hz), 5.70(1H, t, J=5.6 Hz), 2.97 (2H, d, J=6), 2.92–2.85 (1H, m), 2.79–2.70 (2H, m), 2.27–2.18 (4H, m), 2.08–1.95 (6H, m), 1.75–1.38 (18H, m), 1.29 (3H, s), 1.23–1.19 (1H, m), 1.13 (3H, s).

ESIMS (m/z) 422 (M+H)$^+$.

EXAMPLE 15

Preparation of (4β,5α)-12-Hydroxy-N-[(1-phenylcyclohexyl)methyl]podocarpa-8,11,13-trien-16-amide

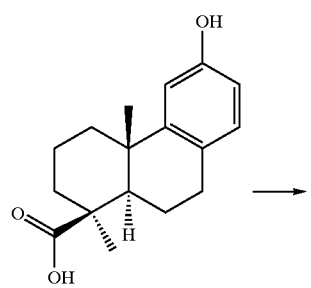

-continued

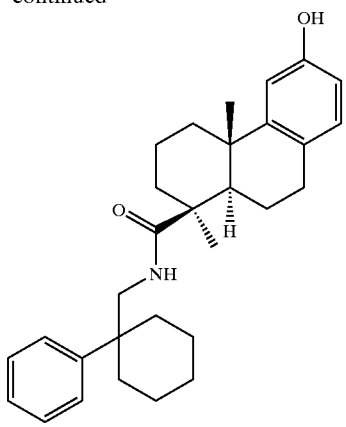

(4β,5α)-12-Hydroxypodocarpa-8,11,13-trien-16-oic acid (483 mg, 1.78 mmol), benzotriazol-1-yloxytris(dimethylamino)phosphonium hexafluorophosphate (786 mg, 1.78 mmol), 1-phenyl-1-cyclohexanemethylamine (370 mg, 1.96 mmol) and diisopropylethylamine (1.24 ml, 7.12 mmol) were dissolved in 5 mL of DMF. The mixture was stirred at RT overnight, then at 70° C. for 2 hours followed by cooling to RT and quenched with ice/water (20 mL). The precipitate of the aqueous solution was collected by filtration and purified by silica gel column chromatography with hexane/ethyl acetate (4:1) as solvent to obtain 600 mg of the titled compound as a white solid.

$^1$HNMR (CDCl$_3$) δ: 7.49–7.37 (4H, m), 7.33–7.20 (1H, m), 6.88 (1H, d, J=8.2 Hz), 6.74 (H, s), 6.62 (1H, d, J=8.2 Hz), 5.17 (1H, t, J=5.2 Hz), 3.50 (1H, dd, J=13.1, 5.7 Hz), 3.33 (1H, dd, J=13.1, 5.7 Hz ), 2.81–2.51 (2H, m), 2.22–1.82 (5H, m), 1.82–1.54 (6H, m), 1.53–1.37 (6H, m), 1.36–1.24 (1H, m), 1.18 (3H, s), 1.08–1.01 (1H, m), 0.91 (3H, s).

ESIMS (m/z) 446 (M+H)$^+$.

EXAMPLE 16

Preparation of (4β,5α)-N-[(1-Phenylcyclohexyl)methyl]podocarpa-8,11,13-trien-16-amide STEP A: Preparation of Diethyl (4β,5α)-16-oxo-16-{[(1-phenylcyclohexyl)methyl]amino}podocarpa-8,11,13-trien-12-yl phosphate.

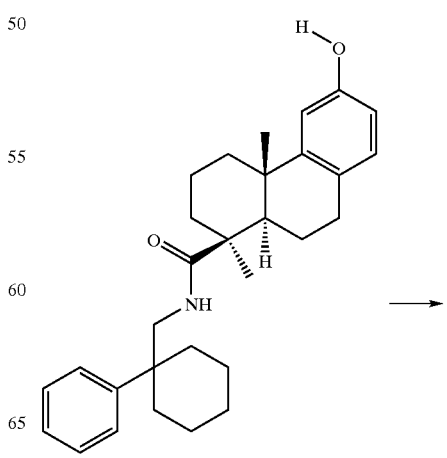

-continued

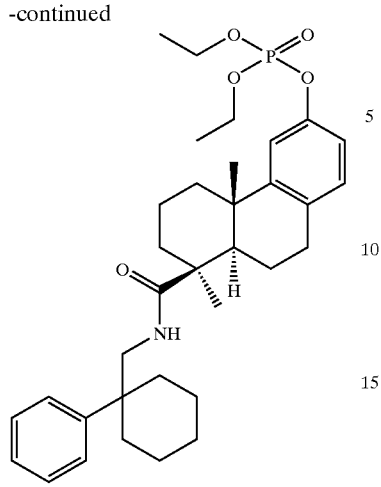

(4β,5α)-12-Hydroxy-N-[(1-phenylcyclohexyl)methyl]podocarpa-8,11,13-trien-16-amide (60 mg, 0.13 mmol) was dissolved in 2 mL dry THF, and 50 mg of NaH was added. The mixture was stirred at RT for 1 hour followed by addition of 33 mg (0.2 mmol) of diethyl phosphorochloridate. The mixture was stirred at RT for 2 hours, quenched with brine (10 ml) and the aqueous solution was extracted with diethyl ether (3×5 ml). The ether extracts were combined and concentrated to dryness. The crude phosphate ester was carried on for the next step without further purification. A small portion of the crude was purified by preparative HPLC (45 min gradient of acetonitrile/water 25–95% at a flow rate of 2 mL/min, Zorbax RX C-8, 9.4 mm×25 cm) to give 4.5 mg of the titled compound which was used without further purification.

$^1$HNMR (CD$_3$OD) δ: 7.56–7.31 (4H, m), 7.25 (1H, t, J=7.2 Hz), 7.10–6.92 (2H, m), 6.92–6.77 (1H, m), 5.74 (1H, t, J=5.2 Hz), 4.18 (4H, q, J=7.3 Hz), 3.53–3.15 (2H, m) 2.88–2.49 (2H, m), 2.28–2.03 (3H, m), 2.03–1.83 (2H, m), 1.79–1.52 (6H, m), 1.52–1.35 (6H, m), 1.32 (6H, t, J=7.2 Hz), 1.12 (3H, s), 0.91 (3H, s).

ESIMS (m/z) 582 (M+H)$^+$.

STEP B: Preparation of (4β,5α)-N-[(1-phenylcyclohexyl)methyl]podocarpa-8,11,13-trien-16-amide.

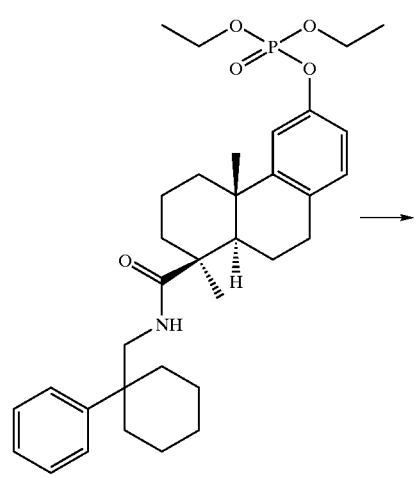

The crude diethyl (4β,5α)-16-oxo-16-{[(1-phenylcyclohexyl)methyl]amino}podocarpa-8,11,13-trien-12-yl phosphate was dissolved in 2 mL of anhydrous diethyl ether and added carefully to 10 mL of liquid ammonia at −78° C. To this mixture was added small pieces of lithium metal (~100 mg) to obtain a deep blue solution. This mixture was stirred at −78° C. for 2 hours. Solid ammonium chloride was added and the blue color turned to white. The mixture was slowly warmed to RT, quenched with water (10 mL) and extracted with diethyl ether (3×5 mL), the extracts were combined, concentrated, and purified by silica gel column chromatography with ethyl acetate/hexane (5:1) as solvent to afford 31 mg of the titled compound as amorphous powder.

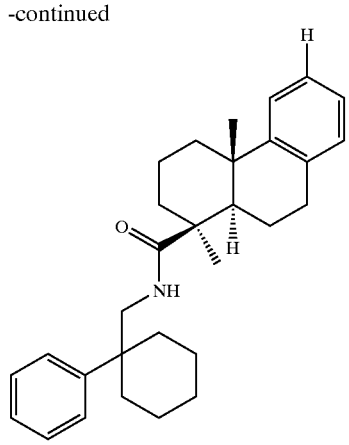

$^1$HNMR (CD$_3$OD) δ: 7.51–7.30 (4H, m), 7.24 (1H, t, J=7.2 Hz), 7.38(1H, d, J=8.2 Hz), 7.08–6.84 (3H, m), 5.68 (1H, t, J=5.2 Hz), 3.52–3.15 (2H, m), 2.85–2.58 (2H, m), 2.32–2.01 (3H, m), 2.02–1.82 (2H, m), 1.79–1.35 (12H, m), 1.34–1.17 (1H, m), 1.11 (3H, s), 1.08–1.04 (1H, m), 0.91 (3H, s).

ESIMS (m/z) 430 (M+H)$^+$.

EXAMPLE 17

Preparation of 1-(1-Adamantyl)-3-[(4β,5α)-12-(hydroxy)-16-oxopodocarpa-8,11,13-trien-16-yl]propane-1,3-dione.

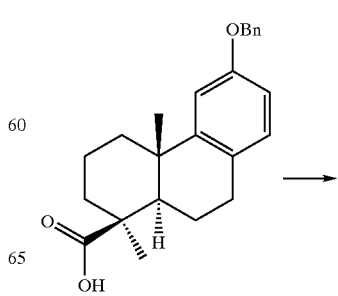

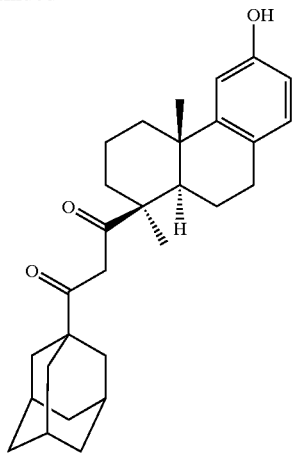

STEP A: Preparation of 2-[(4β,5α)-12-(benxyloxy)-16-oxopodocarpa-8,11,13-trien-16-yl]-1-(1-Adamantyl)ethan-1-one.

(4β,5α)-12-(Benzyloxy)podocarpa-8,11,13-trien-16-oic acid (8.0, 30 mmol) was added to 750 mL of THF. The suspension was stirred at ambient temperature, and lithium aluminum hydride (3.8 g, 103 mmol) was added slowly. The mixture was heated to reflux under nitrogen for 24 hours. The reaction mixture was quenched by addition of saturated potassium tartrate (250 mL), and extracted with ethyl acetate (3×150 mL). The organic layers were combined, washed with water (2×200 mL), brine (150 mL), dried over anhydrous magnesium sulfate, and concentrated to dryness, affording 7.5 g of crude alcohol (100%). This alcohol (1.0 g, 4 mmol) was dissolved in 30 mL of methylene chloride, then tetraprophylammonium peruthenate (53 mg, 0.45 mmol) and 4-methylmorpholine (0.4 g, 0.11 mmol) were added. After stirring for 3 hours at ambient temperature, the reaction was quenched by addition of saturated sodium bicarbonate solution (50 mL). The organic layer was washed with water (2×20 mL), brine (25 mL), dried over anhydrous magnesium sulfate, and evaporated to dryness to afford 0.9 g of crude aldehyde (91%). This crude aldehyde (0.9 g, 0.36 mmol) was dissolved in 50 mL of THF and methyl magnesium bromide (0.18 mL, 3M in diethyl ether) was added. The reaction mixture was stirred for 3 hours at ambient temperature, quenched by addition of saturated ammonium chloride solution (20 mL), and extracted with diethyl ether (2×20 mL). The organic layers were combined, washed with water (2×20 mL) and brine (25 mL), dried over anhydrous magnesium sulfate, and concentrated to dryness to obtain 0.9 g of crude methyl-alcohol (92%). To a cooled (0° C.) solution of this methyl alcohol (0.9 g, 0.33 mmol) and 4-methylmorpholine (0.36 g, 0.1 mmol) in 40 mL of methylene chloride was added tetrapropylammonium peruthenate (50 mg, 0.43 mmol). The reaction mixture was stirred for 3 hours at ambient temperature, quenched by addition of saturated sodium bicarbonate solution (40 mL). The methylene chloride layer was washed with water (2×25 mL) and brine (30 mL), dried over anhydrous magnesium sulfate, and concentrated to dryness to give 0.7 g of crude methyl ketone (77%). This methyl ketone (80 mg, 0.22 mmol) was dissolved in 5 mL of anhydrous THF, and a solution of 0.5 M potassium bis(trimethylsilyl)amide (0.5 mL, 0.25 mmol) was added. The solution was stirred at −40° C. for 2 hours followed by addition of 1-adamantanecarboxylic chloride (50 mg, 0.24 mmol) in 1 mL of THF. Stirring was continued at −40° C. for 2 hours, then at ambient temperature overnight. The mixture was concentrated to dryness and purified by preparative HPLC (45 min gradient of acetonitrile/water 25–95% at a flow rate of 15 mL/min, Zorbax RX C-8, 21.2 mm×25 cm) to obtain 54 mg of the titled compound (47%).

$^1$HNMR (CDCl$_3$) δ:7.46–7.31 (5H, m), 6.98 (1H, d, J=8.4 Hz), 6.92 (1H, d, J=2.8 Hz), 6.75 (1H, dd, J=8.4, 2.8 Hz), 5.01 (2H, s), 4.66 (1H, d, J=2.4 Hz), 2.90–2.68 (2H, m), 2.26–2.18 (1H, m), 2.09–1.94 (10H, m), 1.75–1.53 (10H, m), 1.53–1.45 (1H, m), 1.31 (3H, s), 1.17 (3H, s).

ESIMS (m/z) 525(M+H)$^+$.

STEP B: Preparation of 2-[(4β,5α)-12-(hydroxy)-16-oxopodocarpa-8,11,13-trien-16-yl]-1-(1-Adamantyl)ethan-1-one.

To solution of 2-[(4β,5α)-12-(benxyloxy)-16-oxopodocarpa-8,11,13-trien-16-yl]-1-(1-Adamantyl)ethan-1-one (15 mg, 0.028 mmol) in methanol (2 mL) was added 2 mg of palladium on carbon (10%, dry). The suspension was stirred under atmospheric hydrogen at ambient temperature for 4 hours and filtered. The filtrate was concentrated to dryness and purified by preparative HPLC (45 min gradient of acetonitrile/water 25–95% at a flow rate of 2 mL/min, Zorbax RX C-8, 9.4 mm×25 cm) to obtain 5.3 mg (yield, 44%) of the titled compound.

$^1$H NMR (CDCl$_3$) δ: 6.92 (1H, d, J=8.3 Hz), 6.77 (1H, d, J=2.8 Hz), 6.62 (1H, dd, J=8.3, 2.8 Hz), 5.05 (1H, d, J=2.3 Hz), 4.66 (1H, d, J=2.3 Hz), 2.94–2.78 (1H, m), 2.78–2.59 (1H, m), 2.28–2.17 (1H, m), 2.14–2.02 (5H, m), 2.02–1.93 (5H, m), 1.91–1.36 (11H, m), 1.34 (3H, s), 1.17 (3H, s).

ESIMS (m/z) 435 (M+H)$^+$.

The following compounds (Examples 18–25) were prepared according to the methods described above:

EXAMPLE 18

(4β,5α)-N-[1-(1-Adamantyl)ethyl]-12-hydroxypodocarpa-8,11,13-trien-16-amide

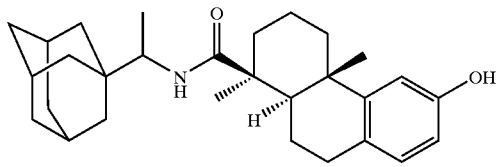

$^1$H NMR (CDCl$_3$) δ: 6.92 (1H, d, J=8.0 Hz), 6.77 (1H, d, J=2.4 Hz), 6.62 (1H, dd, J=8.0, 2.4 Hz), 5.56 (1H, t, J=9.6 Hz), 3.76–3.69 (1H, m), 2.9–2.67 (2H, m), 1.29 (3H, s), 1.16, 1.15 (3H, ss), 1.04, 1.00 (3H, dd, J=6.8 Hz).

ESIMS (m/z) 436 (M+H)$^+$.

EXAMPLE 19

(4β,5α)-N-(2-Adamantyl)-12-hydroxypodocarpa-8,11,13-trien-16-amide

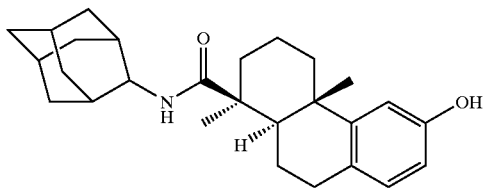

$^1$H NMR (CDCl$_3$) δ: 6.94 (1H, d, J=8.2 Hz), 6.77 (1H, d, J=2.5 Hz), 6.63 (1H, dd, J=8.2, 2.5 Hz), 6.07 (1H, d, J=7.6

Hz), 4.11 (1H, d, J=7.6 Hz), 2.97–2.67 (2H, m), 2.37–2.18 (3H, m), 2.18–1.53 (26H, m), 1.31 (3H, s), 1.23–1.19 (1H, m), 1.16 (3H, s).

ESIMS (m/z) 408 (M+H)⁺.

EXAMPLE 20

(4β,5α)-N-(1-Adamantyl)-12-hydroxypodocarpa-8,11,13-trien-16-amide

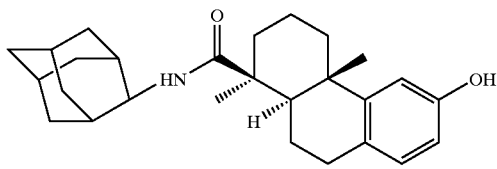

¹H NMR (CDCl₃) δ: 6.89 (1H, d, J=8.0 Hz), 6.75 (1H, d, J=2.0 Hz), 6.60 (1H, dd, J=8.0, 2.0 Hz), 5.38 (1H, brs), 2.87–2.67 (2H, m), 1.23 (3H, s), 1.17 (3H, s).

ESIMS (m/z) 408 (M+H)⁺.

EXAMPLE 21

(4β,5α)-12-Hydroxy-N-[(1R,2R,3R,5S)-2,6,6-trimethylbicyclo[3.1.1]hept-3-yl]podocarpa-8,11,13-trien-16-amide

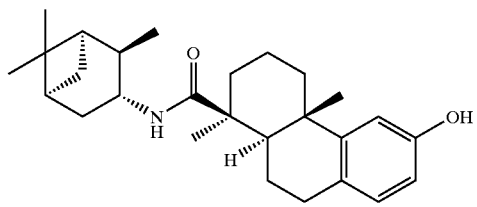

¹H NMR (CDCl₃) δ: 6.87 (1H, d, J=8.0 Hz), 6.79 (1H, d, J=2.0 Hz), 6.60 (1H, dd, J=8.0, 2.0 Hz), 5.59 (1H, d, J=7.5), 4.31 (1H, m), 1.28 (3H, s), 1.23 (3H, s), 1.18 (3H, s), 1.13 (3H, d, J=7.2 Hz), 1.05 (3H, s), 0.85 (1H, d, J=9.6 Hz).

ESIMS (m/z) 410 (M+H)⁺.

EXAMPLE 22

(4β,5α)-16-Oxo-16-(4-phenylazepan-1-yl)podocarpa-8,11,13-trien-12-ol

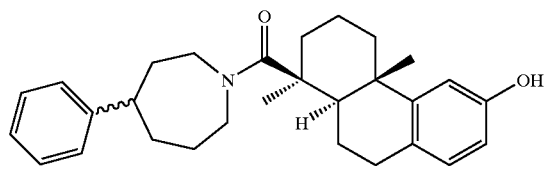

¹H NMR (CD₃OD) δ: 7.36–7.08 (5H, m), 6.80 (1H, d, J=8.4 Hz), 6.69 (1H, d, J=1.6 Hz), 6.49 (1H, dd, J=8.4, 1.6 Hz), 3.98–3.72 (2H, m), 3.72–3.57 (1H, m), 3.57–3.42 (1H, m), 2.87–2.48 (10H, m), 2.35–1.60 (14H, m), 1.42, 1.41 (3H, ss), 1.20, 1.17 (3H, ss).

ESIMS (m/z) 432 (M+H)⁺.

EXAMPLE 23

Ethyl 4-benzyl-1-[(4β,5α)-12-hydroxy-16-oxopodocarpa-8,11,13-trien-16-yl]piperidine-4-carboxylate

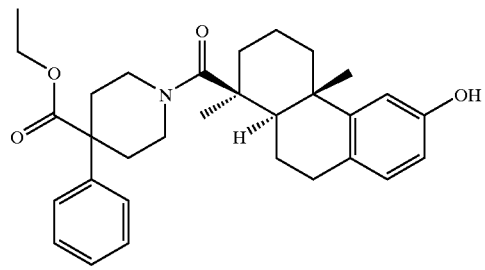

¹HNMR (CD₃OD) δ: 7.28–7.08 (5H, m), 6.80 (1H, d, J=8.4 Hz), 6.65 (1H, d, J=1.6 Hz), 6.49 (1H, dd, J=8.4, 1.6 Hz), 4.19 (2H, m), 4.12 (2H, q, J=7.5), 1.28 (3H, s), 1.20 (3H, t, J=7.5), 1.07 (3H, s).

ESIMS (m/z) 504 (M+H)⁺.

EXAMPLE 24

(4β,5α)-16-[3-(2-Methylphenyl)piperidin-1-yl]-16-oxopodocarpa-8,11,13-trien-12-ol

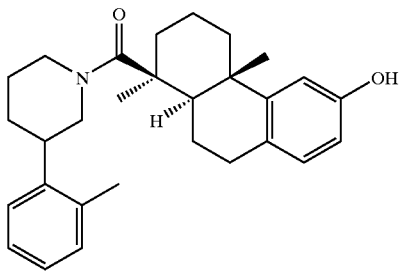

¹HMNR (CDCl₃) δ: 7.31–7.09 (4H, m), 6.90 (1H, d, J=8.3 Hz), 6.78 (1H, d, J=2.5 Hz), 6.62 (1H, dd, J=8.3, 2.5 Hz), 4.54–4.42 (2H, m), 3.04–2.75 (2H, m), 2.75–2.59 (1H, m), 2.49–2.33 (4H, m), 1.27–2.09 (2H, m), 2.09–1.95 (1H, m), 1.90–1.80 (1H, m), 1.80–1.62 (3H, m), 1.24 (3H, s), 1.13 (3H, s).

ESIMS (m/z) 432 (M+H)⁺.

EXAMPLE 25

(4β,5α)-16-(4-Benzylpiperidin-1-yl)-16-oxopodocarpa-8,11,13-trien-12-ol

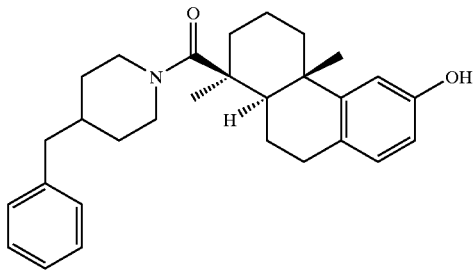

¹HNMR (CDCl₃) δ: 7.41–7.09 (5H, m), 6.91 (1H, d, J=8.5 Hz), 6.78 (1H, d, J=2.6 Hz), 6.62 (1H, dd, J=8.5, 2.6

Hz), 4.48–4.29 (2H, m), 2.95–2.62 (4H, m), 2.59 (2H, d, J=7.1 Hz), 2.50–2.26 (2H, m) 2.26–2.07 (2H, m), 1.90–1.62 (4H, m), 1.56–1.42 (2H, m), 1.40 (3H, s), 1.30–1.22 (2H, m), 1.21 (3H, s), 1.20–1.13 (1H, m).

ESIMS (m/z) 432 (M+H)$^+$.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agents used in the instant invention as indicated above. Likewise, the specific pharmacological responses observed may vary according to and depending upon the particular active compound selected or whether there are present pharmaceutical carriers, as well as the type of formulation employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of Formula I:

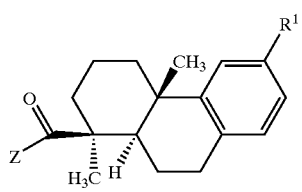

and the pharmaceutically acceptable salts and esters thereof, wherein

Z is selected from the group consisting of:
 (a) Formula Ia

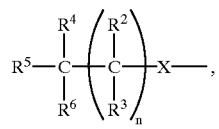

and
 (b) Formula Ib

wherein Formula Ib represents a saturated heterocyclic ring containing one tertiary nitrogen atom and 5 or 6 carbon atoms, wherein each carbon atom is independently unsubstituted or substituted with at least one substituent selected from the group consisting of:
 (i) —$C_{1-4}$ alkyl,
 (ii) phenyl, unsubstituted or substituted with at least one —$C_{1-4}$ alkyl substituent,
 (iii) —$CH_2$-phenyl, wherein phenyl is unsubstituted or substituted with at leant one —$C_{1-4}$ alkyl substituent,
 (iv) —COOH and
 (v) —COO$C_{1-4}$ alkyl;

X is selected from the group consisting of:
 (a) —NH, and
 (b) —$CH_2$—;

$R^1$ is selected from the group consisting of:
 (a) —H,
 (b) —OH and
 (c) —OC(O)$CH_3$;

$R^2$ and $R^3$ are independently selected from the group consisting of:
 (a) —H and
 (b) —$C_{1-4}$ alkyl,
 or $R^2$ and $R^3$ together represent =O;

n is an integer selected from zero and 1;

$R^4$ and $R^5$ represent moieties selected from those defined in the following groups:
 (a) $R^4$ and $R^5$ are independently selected from the group consisting of
  (i) —H and
  (ii) phenyl, unsubstituted or substituted with a group selected from halo, —$C_{1-4}$ alkyl and —O—$C_{1-4}$ alkyl,
 (b) $R^4$ and $R^5$ together represent —$(CH_2)_m$— which joins together with the carbon in Formula Ia to which $R^4$ and $R^5$ are commonly attached to form a cycloalkyl ring, and wherein m is an integer selected from 2 through 5,
 (c) $R^4$ and $R^5$ are each alkyl groups joined together with the carbon in Formula Ia to which they are commonly attached to form a carbon-bridged polycycloalkyl ring system selected from isopinylcampheyl and adamantyl, wherein the ring system is unsubstituted or substituted with —$C_{1-4}$ alkyl,
 (d) $R^4$, $R^5$ and $R^6$ are each alkyl groups joined together with the carbon in Formula Ia to which they are commonly attached to form a carbon-bridged polycycloalkyl ring system which is adamantyl, wherein the ring system is unsubstituted or substituted with —$C_{1-4}$ alkyl, and
 (e) $R^4$, $R^5$ and $R^6$ together with the carbon in Formula Ia to which they are commonly attached represent

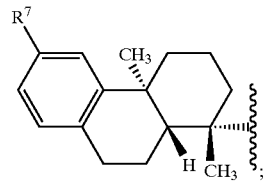

provided $R^6$ is not joined together with $R^4$ and $R^5$ as described above, then $R^6$ is selected from the group consisting of:
 (a) —H and
 (b) phenyl, unsubstituted or substituted with a group selected from halo, —$C_{1-4}$ alkyl and —O—$C_{1-4}$ alkyl,
 except that when $R^4$ and $R^5$ are each alkyl groups joined together with the carbon in Formula Ia to which they are commonly attached to form a carbon-bridged polycycloalkyl ring system, then $R^6$ is —H;

$R^7$ is selected from the group consisting of:
(a) —H,
(b) —OH and
(c) —OC(O)CH$_3$; and provided that when n is 1, and $R^2$ and $R^3$ together represent =O, $R^4$, $R^5$ and $R^6$ together with the carbon in Formula I to which they are commonly attached represent

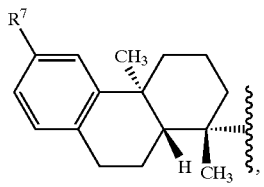

and $R^1$ is —OC(O)CH$_3$ and $R^7$ is —OC(O)CH$_3$, then X is not —O—.

2. The compound of claim 1 wherein Z is Formula Ia.
3. The compound of claim 2 wherein X is —NH—.
4. The compound of claim 3 selected from the group consisting of those wherein $R^1$ and Z are defined as follows:

| | $R^1$ | Z |
|---|---|---|
| (a) | —OH | 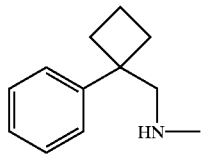 |
| (b) | —OAc | 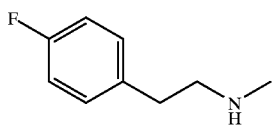 |
| (c) | —OH | 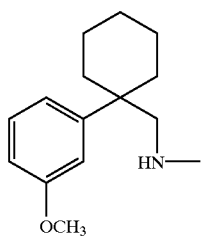 |
| (d) | —OH | 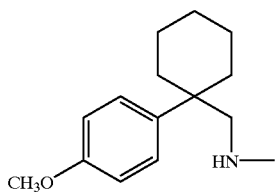 |
| (e) | —OH | 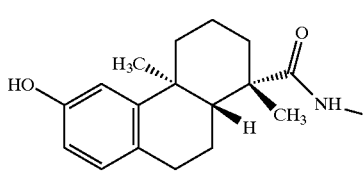 |

-continued

| | $R^1$ | Z |
|---|---|---|
| (f) | —OH |  |
| (g) | —OH | 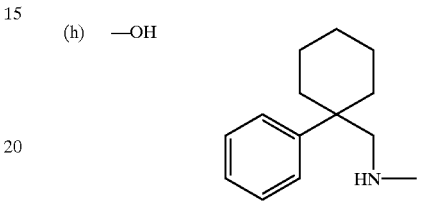 |
| (h) | —OH | 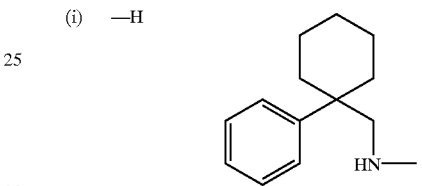 |
| (i) | —H | 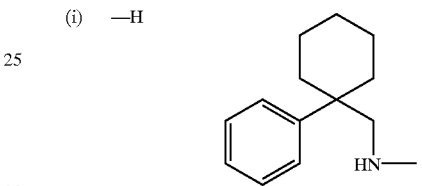 |
| (j) | —OH | 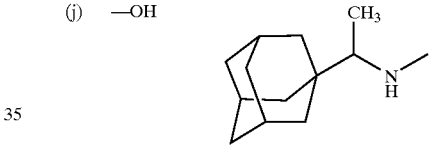 |
| (k) | —OH | 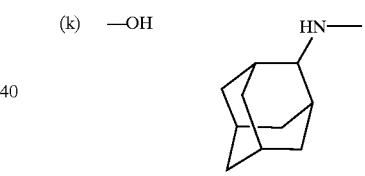 |
| (l) | —OH | 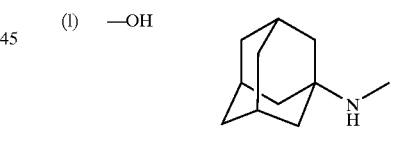 |
| (m) | —OH | 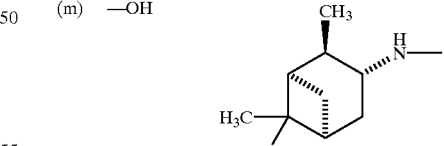 |

5. The compound of claim 3 wherein n is one, $R^4$ and $R^5$ together represent —(CH$_2$)$_m$— which joins together with the carbon in Formula Ia to which $R^4$ and $R^5$ are commonly attached to form a cycloalkyl ring, and wherein m is an integer selected from 3 through 5, and $R^6$ is phenyl, unsubstituted or mono-substituted with a group selected from halo, —C$_{1-4}$ alkyl and —O—C$_{1-4}$ alkyl.

6. The compound of claim 5 selected from the group consisting of those wherein $R^1$ and Z are defined as follows:

| | R¹ | Z |
|---|---|---|
| (a) | —OH | [1-benzyl-cyclobutyl-methylamino group] |
| (b) | —OH | [1-(3-methoxyphenyl)cyclohexyl-methylamino group] |
| (c) | —OH | [1-(4-methoxyphenyl)cyclohexyl-methylamino group] |
| (d) | —OH | [1-phenylcyclohexane-carboxamide group] |
| (e) | —OH | [1-phenylcyclohexyl-methylamino group] |
| (f) | —H | [1-phenylcyclohexyl-methylamino group] |

7. The compound of claim 2 wherein X is —CH$_2$—.

8. The compound of claim 7 selected from the group consisting of those wherein R¹ and Z are defined as follows:

| | R¹ | Z |
|---|---|---|
| (a) | —OH | [1-adamantyl propanoyl group] |

| | R¹ | Z |
|---|---|---|
| (b) | —OH | [1-adamantyl propanoyl group] |

9. The compound of claim 2 wherein R² and R³ together represent =O; and R⁴, R⁵ and R⁶ together with the carbon in Formula Ia to which they are commonly attached represent:

[podocarpane-type tricyclic structure with R⁷ and CH₃ groups]

10. The compound of claim 9 selected from the group consisting of those wherein R¹ and Z are defined as follows:

| | R¹ | Z |
|---|---|---|
| (a) | —OH | [hydroxy-podocarpane carboxamide structure] / [hydroxy-podocarpane methyl ester structure] |
| (b) | —OH | [hydroxy-podocarpane methyl ester structure] |

11. The compound of claim 1 wherein Z is Formula Ib.

12. The compound of claim 11 selected from the group consisting of those wherein R¹ and Z are defined as follows:

| | R¹ | Z |
|---|---|---|
| (a) | —OH | [4-phenyl-1-methyl-azepane group] |

-continued

| | R¹ | Z |
|---|---|---|
| (b) | —OH | 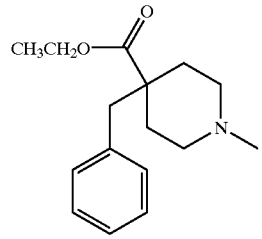 |
| (c) | —OH | 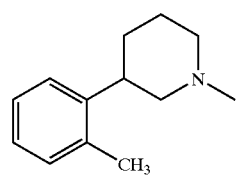 |
| (d) | —OH | 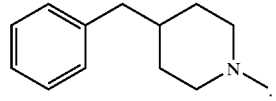 |

13. The compound of claim 11 wherein Formula Ib is a saturated seven-membered heterocyclic ring containing one tertiary nitrogen atom and six carbon atoms, wherein each carbon atom is independently unsubstituted or mono-substituted with a substituent selected from the group consisting of: (i) —$C_{1-4}$ alkyl, (ii) phenyl, unsubstituted or substituted with at least one —$C_{1-4}$ alkyl substituent, (iii) —$CH_2$-phenyl, wherein phenyl is unsubstituted or substituted with at least one —$C_{1-4}$ alkyl substituent, (iv) —COOH and (v) —COO$C_{1-4}$ alkyl.

14. A method for treating dyslipidemia comprising administering a therapeutically effective amount of a compound of claim 1 to a patient in need thereof.

15. The method of claim 14 wherein the dyslipidemia is depressed plasma HDL cholesterol level.

16. A method for treating atherosclerosis comprising administering a therapeutically effective amount of a compound of claim 1 to a patient in need thereof.

17. A method for reducing the risk of occurrence of atherosclerosis comprising administering a prophylactically effective amount of a compound of claim 1 to a patient at risk for developing atherosclerosis.

18. A method for reducing the risk of occurrence of an atherosclerotic disease event comprising administering a prophylactically effective amount of a compound of claim 1 to a patient at risk for having an atherosclerotic disease event.

19. A method for removing cholesterol from tissue deposits comprising administering a therapeutically effective amount of a compound of claim 1 to a patient in need thereof.

20. A method for preventing lipid accumulation in tissue deposits comprising administering a prophylactically effective amount of a compound of claim 1 to a patient in need thereof.

21. A pharmaceutical composition comprised of a compound of claim 1 and a pharmaceutically acceptable carrier.

22. A pharmaceutical composition made by combining a compound of claim 1 with a pharmaceutically acceptable carrier.

23. A process for preparing a pharmaceutical composition comprising combining a compound of Formula I with a pharmaceutically acceptable carrier.

24. The compound of claim 1 wherein Z is Formula Ia and $R^6$ is phenyl, unsubstituted or substituted with a group selected from halo, —$C_{1-4}$ alkyl and —O—$C_{1-4}$ alkyl.

25. The compound of claim 1 wherein Z is Formula Ib, and Formula Ib represents a saturated heterocyclic ring containing one tertiary nitrogen atom and 5 or 6 carbon atoms, with at least one substituent selected from the group consisting of:
(i) —$C_{1-4}$ alkyl,
(ii) phenyl, unsubstituted or substituted with at least one —$C_{1-4}$ alkyl substituent,
(iii) —$CH_2$-phenyl, wherein phenyl is unsubstituted or substituted with at least one —$C_{1-4}$ alkyl substituent,
(iv) —COOH and
(v) —COO$C_{1-4}$ alkyl.

26. The compound

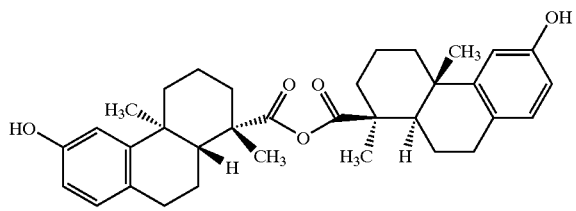

and the pharmaceutically acceptable salts and esters thereof.

* * * * *